US012778688B2

(12) United States Patent
Hendrick et al.

(10) Patent No.: US 12,778,688 B2
(45) Date of Patent: Nov. 3, 2026

(54) CONCENTRIC TUBE APPARATUS FOR MINIMALLY INVASIVE SURGERY

(71) Applicant: Virtuoso Surgical, Inc., Nashville, TN (US)

(72) Inventors: Richard Hendrick, Nashville, TN (US); Neal Dillon, Nashville, TN (US); Evan Blum, Nashville, TN (US); Lauren Branscombe, Nashville, TN (US)

(73) Assignee: Virtuoso Surgical, Inc., Nashville, TN (US)

( * ) Notice: Subject to any disclaimer, the term of this patent is extended or adjusted under 35 U.S.C. 154(b) by 952 days.

(21) Appl. No.: 17/165,315

(22) Filed: Feb. 2, 2021

(65) Prior Publication Data

US 2022/0241029 A1 Aug. 4, 2022

(51) Int. Cl.
*A61B 34/30* (2016.01)
*A61B 17/00* (2006.01)

(52) U.S. Cl.
CPC .... *A61B 34/30* (2016.02); *A61B 2017/00336* (2013.01); *A61B 2034/301* (2016.02)

(58) Field of Classification Search
CPC ........... A61B 2017/00331; A61B 2017/00336; A61B 2017/00353
See application file for complete search history.

(56) References Cited

U.S. PATENT DOCUMENTS

| | | | |
|---|---|---|---|
| 2,397,606 | A | 4/1946 | Hoyle |
| 2,770,813 | A | 11/1956 | Marzillier |
| 2,999,599 | A | 9/1961 | Jentzen |
| 3,042,978 | A | 7/1962 | Charles et al. |

(Continued)

FOREIGN PATENT DOCUMENTS

| | | |
|---|---|---|
| AT | 474496 | 8/2010 |
| CA | 2630061 A1 | 5/2007 |

(Continued)

OTHER PUBLICATIONS

Dupont, P. E. et al., "Design and control of concentric-tube robots", IEEE Transactions on Robotics, 2009, vol. 26, No. 2, pp. 209-225 abstract; pp. 209-212; figures 1-2, 6.

(Continued)

*Primary Examiner* — Martin T Ton
(74) *Attorney, Agent, or Firm* — Holland & Knight LLP; Matthew C. Cox; Forrest S. Tinnin

(57) ABSTRACT

A minimally invasive surgery device includes a guide tube with a highly-curved distal end housed within a channel. The highly-curved distal end is configured with a curvature optimized for improved triangulation in a tissue workspace. The highly-curved distal end of the guide tube extends from a curved channel inside an endoscopic device on a surgical robot. The combination of the curved channel and the highly-curved distal end of the guide tube provides improved maneuverability in the workspace. In some embodiments, the highly-curved distal end includes nitinol and shapeset to a desired curvature. The highly-curved distal ends may be curved to achieve a stable shape with repeatable performance. In some embodiments, each first and second guide tube includes a double-curvature configuration.

20 Claims, 15 Drawing Sheets

(56) References Cited

U.S. PATENT DOCUMENTS

| | | | |
|---|---|---|---|
| 3,046,572 | A | 7/1962 | Charles et al. |
| 3,088,127 | A | 5/1963 | Eames |
| 3,115,819 | A | 12/1963 | Mahlmeister et al. |
| 3,170,417 | A | 2/1965 | Avidiya |
| 3,451,183 | A | 6/1969 | Lespagnol et al. |
| 3,462,892 | A | 8/1969 | Meyer |
| 3,492,767 | A | 2/1970 | Abraham |
| 3,514,794 | A | 6/1970 | Giancarlo |
| 3,623,284 | A | 11/1971 | Meyer |
| 3,660,591 | A | 5/1972 | Schultz et al. |
| 3,694,830 | A | 10/1972 | Koller |
| 3,727,753 | A | 4/1973 | Starr et al. |
| 3,742,932 | A | 7/1973 | Greenspan |
| 3,748,010 | A | 7/1973 | Garte |
| 3,762,398 | A | 10/1973 | Schefke et al. |
| 3,846,853 | A | 11/1974 | Jacobsson |
| 3,971,078 | A | 7/1976 | Herrera |
| 4,130,123 | A | 12/1978 | Wines et al. |
| 4,181,347 | A | 1/1980 | Clark |
| 4,267,769 | A | 5/1981 | Davis et al. |
| D261,804 | S | 11/1981 | Foster et al. |
| 4,319,794 | A | 3/1982 | Bachor |
| 4,352,991 | A | 10/1982 | Kaufman |
| 4,360,991 | A | 11/1982 | West |
| 4,409,889 | A | 10/1983 | Burleson |
| 4,425,978 | A | 1/1984 | Star |
| 4,427,244 | A | 1/1984 | Castagna |
| 4,569,163 | A | 2/1986 | Long |
| 4,586,759 | A | 5/1986 | Wrobel |
| 4,646,211 | A | 2/1987 | Gallant et al. |
| 4,753,055 | A | 6/1988 | Durham, Jr. |
| 4,789,210 | A | 12/1988 | Weiss et al. |
| 4,935,017 | A | 6/1990 | Sylvanowicz |
| 4,953,327 | A | 9/1990 | Cohodar |
| 5,065,462 | A | 11/1991 | Romano |
| 5,086,527 | A | 2/1992 | Takahashi et al. |
| 5,086,593 | A | 2/1992 | Walentine |
| 5,107,636 | A | 4/1992 | Schindele et al. |
| 5,108,063 | A | 4/1992 | Koerber et al. |
| 5,123,203 | A | 6/1992 | Hiromoto |
| 5,136,737 | A | 8/1992 | Reppas et al. |
| 5,165,770 | A | 11/1992 | Hahn |
| 5,323,565 | A | 6/1994 | Kappers et al. |
| 5,377,371 | A | 1/1995 | Foster |
| 5,448,859 | A | 9/1995 | Walker et al. |
| 5,456,655 | A | 10/1995 | Morris |
| 5,513,574 | A | 5/1996 | Collins |
| 5,592,787 | A | 1/1997 | Ophardt |
| 5,640,816 | A | 6/1997 | Reiland et al. |
| 5,687,717 | A | 11/1997 | Halpern et al. |
| 5,704,892 | A | 1/1998 | Adair |
| 5,727,353 | A | 3/1998 | Getz et al. |
| 5,775,034 | A | 7/1998 | Logue |
| 5,800,002 | A | 9/1998 | Tiedge et al. |
| 5,876,373 | A | 3/1999 | Giba et al. |
| 5,878,536 | A | 3/1999 | Demmitt et al. |
| 5,903,937 | A | 5/1999 | Clarke |
| 5,921,915 | A | 7/1999 | Aznoian et al. |
| 5,966,760 | A | 10/1999 | Gallant et al. |
| 5,991,947 | A | 11/1999 | Lavin et al. |
| 6,006,379 | A | 12/1999 | Hensley |
| 6,036,286 | A | 3/2000 | Krumholz |
| D427,805 | S | 7/2000 | Swensson et al. |
| 6,082,799 | A | 7/2000 | Marek |
| D429,089 | S | 8/2000 | Swensson et al. |
| D430,276 | S | 8/2000 | Swensson et al. |
| 6,096,004 | A | 8/2000 | Meglan et al. |
| 6,096,025 | A | 8/2000 | Borders |
| 6,123,203 | A | 9/2000 | Gibbons |
| 6,209,939 | B1 | 4/2001 | Wacker |
| 6,220,681 | B1 | 4/2001 | Swensson et al. |
| D443,044 | S | 5/2001 | Swensson et al. |
| 6,243,993 | B1 | 6/2001 | Swensson |
| 6,256,936 | B1 | 7/2001 | Swensson et al. |
| 6,325,808 | B1 | 12/2001 | Bernard et al. |
| 6,378,255 | B1 | 4/2002 | Eich et al. |
| D457,249 | S | 5/2002 | Gilbert |
| 6,401,276 | B1 | 6/2002 | Sherman |
| 6,405,491 | B1 | 6/2002 | Gallant et al. |
| D460,537 | S | 7/2002 | Gilbert |
| 6,428,073 | B1 | 8/2002 | Blodgett, Jr. |
| 6,497,442 | B1 | 12/2002 | Wacker |
| 6,637,049 | B2 | 10/2003 | Gallant |
| 6,712,414 | B2 | 3/2004 | Morrow |
| 6,719,384 | B1 | 4/2004 | Parise et al. |
| 6,727,744 | B2 | 4/2004 | Nagaya |
| 6,877,824 | B2 | 4/2005 | Winkless |
| 6,879,141 | B1 | 4/2005 | Ho |
| 6,883,277 | B2 | 4/2005 | Wiechecki et al. |
| 6,978,499 | B2 | 12/2005 | Gallant et al. |
| 6,984,057 | B1 | 1/2006 | Rogers |
| 7,040,057 | B2 | 5/2006 | Gallant et al. |
| 7,065,811 | B2 | 6/2006 | Newkirk et al. |
| 7,090,683 | B2 | 8/2006 | Brock et al. |
| 7,100,967 | B2 | 9/2006 | Shea |
| 7,116,588 | B2 | 10/2006 | Joo |
| 7,174,678 | B2 | 2/2007 | Gallant |
| 7,219,472 | B2 | 5/2007 | Gallant et al. |
| 7,224,209 | B2 | 5/2007 | Hsu |
| 7,392,621 | B2 | 7/2008 | Gallant et al. |
| 7,537,030 | B2 | 5/2009 | Gallant |
| 7,822,458 | B2 | 10/2010 | Webster et al. |
| 7,883,475 | B2 | 2/2011 | Dupont et al. |
| 8,152,756 | B2 | 4/2012 | Webster et al. |
| 8,394,129 | B2 | 3/2013 | Morgenstern et al. |
| 8,602,288 | B2 | 12/2013 | Shelton et al. |
| 8,715,226 | B2 | 5/2014 | Webster et al. |
| 8,747,389 | B2 | 6/2014 | Goldfarb et al. |
| 8,886,331 | B2 | 11/2014 | Labadie et al. |
| 9,089,256 | B2 | 7/2015 | Tognaccini et al. |
| 9,289,899 | B2 | 3/2016 | Rucker et al. |
| 9,492,927 | B2 | 11/2016 | Diolaiti et al. |
| 9,901,412 | B2 | 2/2018 | Lathrop et al. |
| 10,149,694 | B2 | 12/2018 | Lathrop et al. |
| 10,238,457 | B2 | 3/2019 | Herrell et al. |
| 10,307,214 | B2 | 6/2019 | Lathrop et al. |
| 10,548,628 | B2 | 2/2020 | Swaney et al. |
| 10,653,491 | B2 | 5/2020 | Lathrop et al. |
| 10,737,398 | B2 | 8/2020 | Remirez et al. |
| 10,803,662 | B2 | 10/2020 | Alterovitz et al. |
| 10,846,928 | B2 | 11/2020 | Alterovitz et al. |
| 10,912,620 | B2 | 2/2021 | Mahoney et al. |
| 2002/0026753 | A1 | 3/2002 | Ray |
| 2002/0029013 | A1 | 3/2002 | Paskar |
| 2002/0087048 | A1 | 7/2002 | Brock et al. |
| 2002/0104271 | A1 | 8/2002 | Gallant |
| 2002/0120178 | A1 | 8/2002 | Tartaglia et al. |
| 2003/0019165 | A1 | 1/2003 | Gallant et al. |
| 2003/0109852 | A1 | 6/2003 | Peterson et al. |
| 2003/0139756 | A1 | 7/2003 | Brustad |
| 2003/0144657 | A1 | 7/2003 | Bowe et al. |
| 2003/0182885 | A1 | 10/2003 | Gresham et al. |
| 2004/0015151 | A1 | 1/2004 | Chambers |
| 2004/0019996 | A1 | 2/2004 | Singer |
| 2004/0138529 | A1 | 7/2004 | Wiltshire et al. |
| 2004/0160074 | A1 | 8/2004 | Shea |
| 2004/0163327 | A1 | 8/2004 | Cash |
| 2004/0199996 | A1 | 10/2004 | Newkirk et al. |
| 2004/0237202 | A1 | 12/2004 | Gallant et al. |
| 2005/0154379 | A1 | 7/2005 | Mcgowan et al. |
| 2005/0171601 | A1 | 8/2005 | Cosgrove et al. |
| 2006/0073713 | A1 | 4/2006 | Chance |
| 2007/0060879 | A1 | 3/2007 | Weitzner et al. |
| 2007/0197896 | A1 | 8/2007 | Moll et al. |
| 2007/0199262 | A1 | 8/2007 | Kern et al. |
| 2007/0199263 | A1 | 8/2007 | Kern et al. |
| 2007/0204401 | A1 | 9/2007 | Heimbrock |
| 2007/0251165 | A1 | 11/2007 | Kern et al. |
| 2007/0287992 | A1 | 12/2007 | Diolaiti et al. |
| 2007/0289225 | A1 | 12/2007 | Kern et al. |
| 2008/0027464 | A1 * | 1/2008 | Moll ..................... A61B 34/30 606/130 |
| 2008/0051631 | A1 | 2/2008 | Dejima et al. |
| 2008/0064921 | A1 | 3/2008 | Larkin et al. |

(56) References Cited

U.S. PATENT DOCUMENTS

| | | | | |
|---|---|---|---|---|
| 2008/0071288 | A1 | 3/2008 | Larkin et al. | |
| 2008/0103491 | A1 | 5/2008 | Omori et al. | |
| 2008/0154389 | A1 | 6/2008 | Smith et al. | |
| 2008/0195041 | A1 | 8/2008 | Goldfarb et al. | |
| 2008/0215067 | A1* | 9/2008 | Dupont | A61B 17/062 606/130 |
| 2008/0243064 | A1 | 10/2008 | Stahler et al. | |
| 2009/0171271 | A1 | 7/2009 | Webster et al. | |
| 2009/0312645 | A1* | 12/2009 | Weitzner | A61B 1/018 600/106 |
| 2010/0113874 | A1 | 5/2010 | Quirini et al. | |
| 2010/0268241 | A1 | 10/2010 | Flom et al. | |
| 2010/0274087 | A1 | 10/2010 | Diolaiti et al. | |
| 2010/0280449 | A1 | 11/2010 | Alvarez et al. | |
| 2011/0015490 | A1 | 1/2011 | Trovato et al. | |
| 2011/0029071 | A1 | 2/2011 | Zlotnick et al. | |
| 2011/0071508 | A1 | 3/2011 | Duval et al. | |
| 2011/0083672 | A1 | 4/2011 | Webster et al. | |
| 2011/0166514 | A1 | 7/2011 | Trovato et al. | |
| 2011/0238083 | A1* | 9/2011 | Moll | A61B 34/25 606/130 |
| 2011/0251455 | A1* | 10/2011 | Popovic | A61B 34/20 600/104 |
| 2011/0282357 | A1 | 11/2011 | Rogers et al. | |
| 2012/0029288 | A1* | 2/2012 | Greenblatt | A61B 17/3421 600/140 |
| 2012/0041263 | A1 | 2/2012 | Sholev | |
| 2012/0071822 | A1 | 3/2012 | Romo et al. | |
| 2012/0080503 | A1 | 4/2012 | Woodard et al. | |
| 2012/0221011 | A1 | 8/2012 | Larkin et al. | |
| 2013/0035537 | A1 | 2/2013 | Wallace et al. | |
| 2013/0066358 | A1* | 3/2013 | Nalluri | A61F 11/202 606/199 |
| 2013/0123802 | A1 | 5/2013 | Comber et al. | |
| 2013/0324914 | A1 | 12/2013 | Valdastri et al. | |
| 2014/0005640 | A1 | 1/2014 | Shelton et al. | |
| 2014/0005680 | A1 | 1/2014 | Shelton et al. | |
| 2014/0005708 | A1 | 1/2014 | Shelton, IV | |
| 2014/0005718 | A1 | 1/2014 | Shelton et al. | |
| 2014/0025089 | A1 | 1/2014 | Sholev | |
| 2014/0180309 | A1 | 6/2014 | Seeber et al. | |
| 2014/0221750 | A1 | 8/2014 | Weitzner | |
| 2014/0257327 | A1* | 9/2014 | Olson | A61B 34/30 606/130 |
| 2014/0276949 | A1 | 9/2014 | Staunton et al. | |
| 2014/0277105 | A1 | 9/2014 | Lathrop et al. | |
| 2014/0277334 | A1 | 9/2014 | Yu et al. | |
| 2015/0066022 | A1 | 3/2015 | Shelton et al. | |
| 2015/0080650 | A1 | 3/2015 | Dejima et al. | |
| 2015/0080907 | A1 | 3/2015 | Herrell et al. | |
| 2015/0142012 | A1 | 5/2015 | Lohmeier et al. | |
| 2015/0223832 | A1 | 8/2015 | Swaney et al. | |
| 2015/0246205 | A1* | 9/2015 | Schaeffer | A61B 1/05 604/95.04 |
| 2016/0067450 | A1 | 3/2016 | Kowshik | |
| 2016/0095505 | A1 | 4/2016 | Johnson et al. | |
| 2016/0106508 | A1 | 4/2016 | Lathrop et al. | |
| 2016/0199057 | A1 | 7/2016 | Parsons et al. | |
| 2016/0206347 | A1 | 7/2016 | Bar et al. | |
| 2016/0296267 | A1 | 10/2016 | Neimat et al. | |
| 2016/0346513 | A1 | 12/2016 | Swaney et al. | |
| 2017/0027656 | A1 | 2/2017 | Robert et al. | |
| 2017/0095299 | A1 | 4/2017 | Webster, III et al. | |
| 2017/0095300 | A1 | 4/2017 | Devengenzo et al. | |
| 2017/0128055 | A1 | 5/2017 | Hartley et al. | |
| 2017/0143436 | A1 | 5/2017 | Lathrop et al. | |
| 2017/0164934 | A1 | 6/2017 | Hartley et al. | |
| 2017/0245889 | A1 | 8/2017 | Herrell et al. | |
| 2017/0273703 | A1 | 9/2017 | Ding et al. | |
| 2017/0333275 | A1 | 11/2017 | Itkowitz et al. | |
| 2017/0348063 | A1 | 12/2017 | Braun et al. | |
| 2017/0367782 | A1 | 12/2017 | Schuh et al. | |
| 2018/0028054 | A1 | 2/2018 | Hoffman et al. | |
| 2018/0168762 | A1 | 6/2018 | Scheib et al. | |
| 2018/0256015 | A1* | 9/2018 | Johnson | A61B 1/0055 |
| 2019/0000580 | A1 | 1/2019 | Scheib et al. | |
| 2019/0015166 | A1 | 1/2019 | Mahoney et al. | |
| 2019/0083749 | A1 | 3/2019 | Swaney et al. | |
| 2019/0090971 | A1 | 3/2019 | Peine | |
| 2019/0133705 | A1 | 5/2019 | Riojas et al. | |
| 2019/0175288 | A1 | 6/2019 | Herrell et al. | |
| 2019/0314112 | A1 | 10/2019 | Wellborn et al. | |
| 2019/0328473 | A1 | 10/2019 | Chassot et al. | |
| 2020/0046441 | A1* | 2/2020 | Liu | A61B 34/30 |
| 2020/0069331 | A1 | 3/2020 | Swaney et al. | |
| 2020/0222079 | A1 | 7/2020 | Swaney et al. | |
| 2020/0289229 | A1 | 9/2020 | Denlinger et al. | |
| 2020/0352658 | A1 | 11/2020 | Johnson et al. | |
| 2020/0397516 | A1 | 12/2020 | Hendrick et al. | |
| 2020/0406002 | A1 | 12/2020 | Romo et al. | |
| 2021/0393338 | A1 | 12/2021 | Graetzel et al. | |
| 2022/0015825 | A1 | 1/2022 | Merryman et al. | |
| 2022/0193412 | A1 | 6/2022 | Bruns et al. | |

FOREIGN PATENT DOCUMENTS

| | | | |
|---|---|---|---|
| CN | 101351236 | A | 1/2009 |
| DE | 3929654 | A1 | 3/1990 |
| DE | 602007007995 | | 9/2010 |
| DE | 112020001961 | T5 | 12/2021 |
| EP | 0339799 | A2 | 11/1989 |
| EP | 0970663 | A1 | 1/2000 |
| EP | 1459692 | A1 | 9/2004 |
| EP | 1014870 | B1 | 5/2007 |
| EP | 1973595 | A2 | 10/2008 |
| EP | 2136698 | A1 | 12/2009 |
| EP | 2779923 | A1 | 9/2014 |
| EP | 3200704 | A2 | 8/2017 |
| EP | 3399938 | A1 | 11/2018 |
| EP | 3534822 | A1 | 9/2019 |
| EP | 3706849 | A1 | 9/2020 |
| EP | 4287982 | A1 | 12/2023 |
| GB | 0945279 | A | 12/1963 |
| IT | 1401667 | B1 | 8/2013 |
| JP | 2000-042116 | A | 2/2000 |
| JP | 2002-500530 | A | 1/2002 |
| JP | 2002-191571 | A | 7/2002 |
| JP | 2012-502681 | A | 2/2012 |
| JP | 2012-513277 | A | 6/2012 |
| JP | 4977776 | B2 | 7/2012 |
| JP | 5276987 | B2 | 8/2013 |
| JP | 5550682 | B2 | 7/2014 |
| JP | 5964335 | B2 | 8/2016 |
| JP | 2017-531482 | A | 10/2017 |
| JP | 6290822 | B2 | 3/2018 |
| KR | 10-1385401 | B1 | 4/2014 |
| WO | 98/11524 | A1 | 3/1998 |
| WO | 2004/018029 | A2 | 3/2004 |
| WO | 2007/059233 | A2 | 5/2007 |
| WO | 2008/122997 | A1 | 10/2008 |
| WO | 2010/073135 | A1 | 7/2010 |
| WO | 2012/005834 | A2 | 1/2012 |
| WO | 2012/028557 | A1 | 3/2012 |
| WO | 2013/074970 | A1 | 5/2013 |
| WO | 2014/129672 | A1 | 8/2014 |
| WO | 2015/073943 | A1 | 5/2015 |
| WO | 2015/077584 | A2 | 5/2015 |
| WO | 2016/049560 | A1 | 3/2016 |
| WO | 2016/076964 | A2 | 5/2016 |
| WO | 2016/191361 | A1 | 12/2016 |
| WO | 2016/191364 | A1 | 12/2016 |
| WO | 2017/059412 | A1 | 4/2017 |
| WO | 2017/120516 | A1 | 7/2017 |
| WO | 2018/084869 | A1 | 5/2018 |
| WO | 2019/089053 | A1 | 5/2019 |
| WO | 2020/106809 | A2 | 5/2020 |
| WO | 2020/163203 | A1 | 8/2020 |
| WO | 2020/215000 | A1 | 10/2020 |
| WO | 2020257679 | A1 | 12/2020 |

(56) References Cited

FOREIGN PATENT DOCUMENTS

| | | | |
|---|---|---|---|
| WO | 2021/183501 | A1 | 9/2021 |
| WO | 2022/169907 | A1 | 8/2022 |

OTHER PUBLICATIONS

PCT/US2022/014989, PCT International Search Report and Written Opinion, dated May 18, 2022, 12 pages.
PCT Application No. PCT/US2006/044386 International Search Report and Written Opinion dated May 15, 2008.
PCT/US2021/062220, International Search Report and Written Opinion, dated Apr. 11, 2022, 9 pages.
Rucker et al., "A Geometrically Exact Model for Externally Loaded Concentric—Tube Continuum Robots" IEEE ransactions on Robotics, vol. 26, No. 5, Oct. 2010.
Rucker et al., "Statics and Dynamics of Continuum Robots with General Tendon Routing and External Loading" EEE Transactions on Robotics, vol. 27, No. 6, Dec. 2011.
Rucker, et al. "Computing Jaccobians and Compliance Matrices for Externally Loaded Continuum Robots," IEEE International Conference of Robots and Automation, Shanghai International Conference Center, May 2011.
Saigal et al., "Economic Costs of Benign Prostatic Hyperplasia in the Private Sector" The Journal of Urology, vol. 173, 2005.
Schieszer, "HoLEP an Option Aller Failed Prior BPH Surgery", Renal and Urology News, Oct. 12, 2012.
Schurizig et al., "A Force Sensing Automated Insertion Tool for cochlear Electrode Implantation" IEEE International Conference on Robotics and Automation, Anchorage, Convention District, 2010.
Shang et al., "An Articulated Universal Joint Based Flexible Access for Robot for Minimally Invasive Surgery" IEEE International Conference on Robotics and Automation, Shanghai International Conference Center, 2011.
Shoham, et al., "Bone-Mounted Miniature Robot for Surgical Procedures: Concept and Clinical Applications" IEEE ransactions on Robotics and Automation, vol. 19, No. 5, Oct. 2003.
Simaan et al., "Design and Integration of a Telerobotic System for Minimally Invasive Surgery of the Throat" The International Journal of Robotics Research, vol. 28, No. 9, pp. 1134-1153, Sep. 2009.
Swaney et al., "Design of a Quadramanual Robot for Single-Nostrik Skull Base Surgery" ASME 2012 5th Annual Dynamic Systems and Control Conference joint with JSME 2012 11th Motion and Vibration Conference, Fort Lauderdale, FL, Oct. 17-19, 2012.
Tooher, et al., "A Systematic Review of Holmium Laser Prostatectomy for Benign Prostatic Hyperplasia" The Journal of Urology, vol. 171, 2004.
Trivedi et al., "Soft Robotics: Biological Inspiration, State of the Art, and Future Research" Applied Biomics and Biomechanics, vol. 5, No. 3, pp. 99-117, Sep. 2008.
Valdastri et al., "Advanced Technologies for Gastrointestinal Endoscopy" Annu. Rev. Biomed. Eng., vol. 14, pp. 397-429, 2012.
Valdastri et al., "Magnetic Air Capsule Robotic System: Proof of Concept of a Novel Approach to Painless Colonscopy" Sug. Endosc., vol. 26, pp. 1238-1246, 2012.
Wampler, Ii, "Manipulator Inverse Kinematic Solutions Based on Vector Formulations and Damped Least-Squares D Methods" IEEE Transactions on Systems, Man and Cybernetics, vol. SMC-16, No. 1 1986.
Wei et al., "Urologic Diseases in America Project: Benign Prostatic Hyperplasia" The Journal of Urology, vol. 173, 2005.
Wei, et al., "Performance Evaluation for Multi-Arm Manipulation of Hollow Suspended Organs" IEEE Transactions on Robotics, vol. 25, No. 1, Feb. 2009.
Weinstein et al., "Transoral Robotic Surgery: Does the Ends Justify the Means?" Otolarngology & Head and Neck Surgery, vol. 17, pp. 126-131, 2009.
Written Opinion of the International Searching Authority, PCT/US06/44386, dated Nov. 23, 2007.
Yamashita et al., "Handheld Laparoscopis Forceps Manipulator Using Multi-Slider Linkage Mechanisms" MICCAI 2004.
Yu, et al., "Practice Patterns in Benign Prostatic Hyperplasia Surgical Therapy: The Dramatic Increase in Minimally Invasive Technologies" The Journal of Urology, vol. 180, pp. 241-245, Jul. 2008.
"Urinary Retention" National Kidney and Urological Diseases Information Clearinghouse, National Institutes of Health, NIH publication No. 08-6089, Dec. 2007.
Vos et al., "Years Lived with Disability (YLDs) for 1160 Sequelae of 289 Diseases and Injuries 1999-2010: A Systematic Analysis of the Global Burden of Disease Study 2010" Lancet, 2012.
Burgner et al., "A Bimanual Teleoperated System for Endonasal Skull Base Surgery" IEEE/RSJ International Conference on Intelligent Robots and Systems, San Fransisco, CA, Sep. 2011.
Burgner et al., "A Telerobotic System for Transnasal Surgery" IEEE/AM SE Transactions of Mechatronics, 2013.
Burgner et al., "Debulking from Within; A Robotic Steerable Cannula for Interacerebral Hemorrhage Evacuation" EEE Transactions on Biomedical Engineering, vol. 60, No. 9, 2013.
Burke et al., "Systematic Review and Meta-Analysis of Transurethral Resection of the Prostate Versus Minimally nvasive Procedures for the Treatment of Benign Prostatic Obstruction" J. Urology, 2009.
Butler et al., "Robotic Neuro-Endoscope with Concentric Tube Augmentation" IEEE/RSJ International Conference Jn Intelligent Robots and Systems, Portugal, 2012.
Chiaverini, "Singularity-Robust Task-Priority Redundancy Resolution for Real-Time Kinematic Control of Robot Manipulators" IEEE Transactions on Robotics and Automation, vol. 13, No. 3, 1997.
Dario, et al., "A Novel Mechatronic Tool for Computer-Assisted Arthroscopy" IEEE Transactions on Information Technology in Biomedicine. vol. 4, No. 1, 2000.
Davies et al., "The Development of a Surgeon Robot for Prostatectomies" Pros. Instn Mech Engrs. vol. 205, 1991.
Emberton et al., "Benign Prostatic Hyperplasia: A Progressive Disease of Aging Men" Elsevier Science, Inc., Urology, vol. 61, 2003.
European Search Report and Search Opinion issued in related Application Serial No 20827391.2 on May 25, 2023.
Fang-Yu Lin et al., "Biometry-based concentric tubes robot for vitreorelinal surgery," 2015 37th Annual International Conference of the IEEE Engineering in Medicine and Biology Society (EMBC), 2015, pp. 5280-5284, doi: 10.1109/EMBC.2015.7319583.
Fenter et al., "The Cost of Treating the 10 Most Prevalent Diseases in Men 50 Years of Age or Older" The American Journal of Managed Care, 2006.
Final Office Action dated Nov. 17, 2009 for U.S. Appl. No. 11/597,850 (11 pages).
Final Office Action issued in related U.S. Appl. No. 17/655,477 on issue Date; Apr. 25, 2024.
Focacci, et al., "Lightweight Hand-Held Robot for Laparoscopic Surgery" IEEE International Conference on Robotics nd Automation, Rome, Italy, 2007.
Gnessin et al., "An Updated on Holmium Laser Enucleation of the Prostate and why ii has Stood the Test of Time" Current Opinion in Urology, 2011.
Goldman et al., "Design and Performance Evaluation of a Minimally Invasive Telerobolic Platform for Transurelhral Surveillance and Intervention", IEEE Transactions on Biomedical Engineering, vol. 60, No. 4, Apr. 2013.
Guess et al., "Cumulative Prevalence of Prostatism Matches the Autopsy Prevalence of Benign Prostatic Hyperplasia" The Prostate, vol. 17, 1990.
H. B. Gilbert et al., "Rapid, Reliable Shape Selling of Superelastic Nilinol for Prototyping Robots," in IEEE Robotics nd Automation Letters, vol. 1, No. 1, pp. 98-105, Jan. 2016, doi: 10.1109/LRA.2015.2507706.
Harris et al., "The Probol- an Active Robot for Prostate Resection" Pros Instn Mech Engrs, vol. 211, Part H, 1997.
Hashimoto et al., "A Tubular Organ Resection Manipulator for Transurelhral Resection of the Prostate" IEEE/RSJ International Conference on Intelligent Robots and Systems, 2004.
International Search Report and Written Opinion dated Dec. 14, 2006 for PCT/US05/18825 (7 pages).

(56) References Cited

OTHER PUBLICATIONS

International Search Report and Written Opinion issued in related Application Serial No. PCT/US05/18824, on Issue Dec. 11, 2006.
International Search Report and Written Opinion issued in related Application Serial No. PCT/US05/19012, on Issue Oct. 2, 2006.
International Search Report and Written Opinion issued in related Application Serial No. PCT/US05/19084, on Issue Mar. 6, 2006.
International Search Report and Written Opinion issued in related Application Serial No. PCT/US05/19085, on Issue Oct. 25, 2006.
International Search Report and Written Opinion issued in related Application Serial No. PCT/US2020/038784 on Sep. 29, 2020.
International Search Report and Written Opinion issued in related Application Serial No. PCT/US2022/071218 on Jun. 20, 2022.
International Search Report and Written Opinion, PCT/US2016/055137, dated Jan. 17, 2017.
International Search Report dated Feb. 6, 2007 for PCT/US05/18825 (7 pages).
International Search Report dated Jul. 27, 2006 for PCT/US05/18974 (7 pages).
Issa et al., "An Assessment of the Diagnosed Prevalence of Disease in Men 50 Years of Age or Older" The American Journal of Managed Care, vol. 14, No. 4.
Kruep et al., "Evaluation of Recent Trends in Treatment Patterns Among Men with Benign Prostatic Hyperplasia" American Journal of Men's Health, http://jmh.sagepub.com/contenl/7/3/214.
Kuo et al., "Holmium Laser Enucleation of the Prostate {HoLEP): A Technical Update" World Journal of Surgical Oncology, vol. 1, No. 6, 2003.
Mandeville et al., "New Advances in Benign Prostallc Hyperplasia: Laser Therapy" Curr Urol Rep, vol. 12, 2011.
Matinfar et al., "Robot-Assisted Skull Base Surgery" 2007 IEEE/RSJ International Conference on the Intelligent Robots and Systems, San Diego, CA, 2007.
Mavudura et al., "Comparison of HoLEP and TURP in Terms of Efficacy in the Early Postoperative Period and Perioperative Morbidity" Urologia Internationalis, 2007.
Mcconnell et al., "The Long-Term Effect of Doxazosin, Finasteride, and Combination Therapy on the Clinical Progression of Benign Prostatic Hyperplasia" The New England Journal of Medicine, vol. 349 No. 25, Dec. 2003.
Miroir et al., "RobOtol: From Design to Evaluation of a Robot for the Middle Ear Surgery" IEEE/RSJ International Conference on Intelligent Robots and Systems, Taipei, Taiwan, Oct. 2010.
Office Action cited in related Japanese Application Serial No. 2021-576267 dated Apr. 17, 2024.
Office Action dated Apr. 15, 2010 for U.S. Appl. No. 11/597,850 (14 pages).
Office Action dated Apr. 3, 2009 for U.S. Appl. No. 11/597,850 (10 pages).
Office Action dated Jan. 11, 2010 for U.S. Appl. No. 11/628,016 (14 pages).
Office Action dated Jul. 8, 2009 for U.S. Appl. No. 11/628,016 (15 pages).
Ok.az.awa et al., "Hand-Held Steerable Needle Device" IEE/ASME Transactions on Mechanics. vol. 10, No. 3, Jun. 2005.
Extended European Search Report issued in related Application Serial No. 22750349.7 on Dec. 16, 2024.
Japanese Office Action issued in related Application Serial No. 2023-544435 on Jul. 3, 2025.

* cited by examiner

CONCENTRIC TUBE APPARATUS FOR MINIMALLY INVASIVE SURGERY

STATEMENT REGARDING FEDERALLY SPONSORED RESEARCH OR DEVELOPMENT

Not Applicable. This invention was made with government support under R44EB024423 and R44HL 140709 from the National Institutes of Health. The government has certain rights in the invention.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

Not Applicable.

REFERENCE TO SEQUENCE LISTING OR COMPUTER PROGRAM LISTING APPENDIX

Not Applicable.

BACKGROUND

The present invention relates to surgical devices and associated methods for performing surgery. More particularly, the present invention relates to tools and methods for minimally invasive surgery using concentric tube assemblies.

Minimally invasive surgery using electromechanical robots is a developing field of medicine. Conventional devices for performing minimally invasive surgery, such as endoscopes and resectoscopes, generally include a distal tip that is inserted through an incision or a natural orifice in a patient's body. The distal tip includes an optical lens which allows a surgeon to see a field of view proximate to the distal tip when placed inside the body. The endoscope will typically have a camera attached to the lens to display the field of view on an operating room monitor. In some applications the endoscope includes a camera installed on the distal tip of the endoscope. The device also includes a narrow working channel extending through the device. One or more elongated surgical tools may be inserted through the working channel. A tool such as a cutting device, a basket or a laser optic may be included on the surgical tool. The distal end of the surgical tool protrudes from the distal tip of the device, thereby allowing the surgeon to visually observe operation of the tool inside the patient's body during an operation.

Conventional surgical tools for use through the narrow working channel of an endoscope or resectoscope are generally limited in size, and are particularly limited in the range of motion and freedom of manipulation of the tool ends extending from the distal end of the endoscope or resectoscope. Curved channels within the endoscope or resectoscope have been proposed as a possible solution to achieve a better range of motion and better ability to manipulate tools in the workspace. However, providing curved channels for passage of surgical tools inside the narrow confines of an endoscope or resectoscope present additional challenges. For example, curved concentric tubes tend to align with the plane of curvature of the channel in which the concentric tube is housed. As a result, a curved tube of a surgical tool positioned inside a curved channel on an endoscope may provide improved range of motion when extended from the distal end of the channel, but such a configuration does not provide an optimal solution when manipulation outside of the plane of curvature of the channel is desired.

Over the past few decades, it has become increasingly clear that entering the body in the most minimally invasive way possible during surgery provides tremendous patient benefit. Minimally invasive surgery is a general term used to describe any surgical procedure that enters the body without large, open incisions. Conventional devices for performing minimally invasive surgery, such as endoscopes and resectoscopes, are generally rigid and include a distal tip that is inserted through an incision in a patient's body or a natural orifice in a patient's body. The distal tip includes an optical lens which allows a surgeon to see a field of view proximate to the distal tip when placed inside the body. The endoscope will typically have a camera attached to it to display the field of view on an operating room monitor. In some applications the endoscope includes a camera installed on the distal tip of the endoscope. The device also includes a working channel extending through the device. One or more elongated surgical tools may be inserted through the working channel. A tool such as a cutting device, a basket or a laser optic may be included on the surgical tool. The distal end of the surgical tool protrudes from the distal tip of the device, thereby allowing the surgeon to visually observe operation of the tool inside the patient's body during an operation.

Minimally invasive surgery includes laparoscopic surgery, which uses a tube to deliver visualization (i.e. an endoscope) and view the surgical field and long, rigid instruments that pass through small ports in the body. In conventional laparoscopic surgery, the endoscope is usually used only for visualization of the surgical field and does not have tools passing through it. The tools are pivoted outside of the body and through the incision port to provide instrument manipulation at the surgical site. The tool manipulation in laparoscopic surgery is created by pivoting long, rigid shafts through ports in the body. For surgery in the insufflated abdomen, chest cavity, pelvis or any other anatomical working volume with sufficient space, this concept often provides an excellent minimally invasive solution for delivering instrument manipulation. However, when the surgical site is down a long, narrow channel, the ability to pivot these long, rigid shafts diminishes. The tool's manipulation ability drops off sharply as access channels become longer and/or narrower.

Minimally invasive surgery also includes endoscopic surgery. While laparoscopic surgery uses endoscopes to provide visualization, endoscopic surgery differs in that the surgical instruments are passed through a working channel of the endoscope tube itself. Some examples of surgical instruments that can be used during endoscopic surgery are scissors, forceps, laser fibers, and monopolar/bipolar cautery. There are both rigid and flexible endoscopes—rigid endoscopes being used in surgeries where a straight, linear path can be taken from the outside of the body to the surgical site, and flexible endoscopes being used where winding through curving anatomy is required. Rigid endoscopes are currently used in almost every area of surgery, including but not limited to neurologic, thoracic, orthopedic, urologic and gynecologic procedures. While rigid endoscopy is currently used in surgeries all over the body, it is not without drawbacks. Tools that operate through the working channel of rigid endoscopes are similar to laparoscopic tools in that they are normally straight, rigid tools. Generally, these tools are also limited to two degrees-of-freedom motion relative to the endoscope: they can insert/retract and rotate axially. Sometimes, the surgeon may have the ability to pivot/tilt the endoscope outside of the body, which makes things particularly challenging, as whenever the endoscope moves, the field of view of the endoscope moves along with it. Also, the surgeon can only get one instrument at a time to the surgical site the vast majority of the time due to the size constraints of the working channel of the endoscope—effectively eliminating the ability for two-handed bimanual tasks. This limitation to a single tool at a time, the constantly changing field of view, limited degrees of freedom, and lack of instrument dexterity at the tip of the endoscope make endoscopic surgery a particularly challenging type of minimally invasive surgery.

Because they are particularly skilled with precision, spatial reasoning, and dexterity, electromechanical surgical robots have great potential to aid in surgical instrument manipulation and is a rapidly developing field of medicine. Surgical robots have gained widespread adoption throughout the world and have been utilized in hundreds of thousands of procedures. The majority of surgical robotic systems designed thus far that aid in instrument manipulation can be generally categorized into pivoted and flexible tools. Pivoted, laparoscopic-like systems such as the widely used da Vinci Xi robot, made by Intuitive Surgical, Inc., gain instrument manipulation in the same way that laparoscopic tools do: by tilting through a port in the body. For surgical applications where tilting or pivoting of the tools is not possible outside of the body, several groups in the research community have been developing robotic systems based on flexible elements. These systems are often referred to as continuum robots, or a continuously bending, robot with an elastic structure. There also exist concentric tube manipulators, which are a class of miniature, needle-sized continuum robot composed of concentric, elastic tubes. Concentric tube robots appear promising in many kinds of minimally invasive surgical interventions that require small diameter robots with articulation inside the body. Examples include surgery in the eye, ear, sinuses, lungs, prostate, brain, and other areas. In most of these applications, higher curvature is generally desirable to enable the robot to turn "tighter corners" inside the human body and work dexterously at the surgical site. In the context of endoscopic surgery, the precurvatures of the concentric tubes determine how closely the manipulators can work to the tip of the endoscope, which is very important during endoscopic surgery.

With traditional endoscopic procedures, surgeons typically hold the endoscope in one hand and the endoscopic instrument in the other, making it generally not possible for the surgeon to simultaneously manipulate two instruments. Due to the human error aspect, whenever the surgeon needs to swap one endoscopic instrument out for another, it can result in awkward and potentially dangerous endoscope movements. Surgeons often, however, need the ability to accurately and simultaneously manipulate two instruments in certain situations—especially when trying to grasp, manipulate, and cut material precisely. Even where endoscopes can accommodate more than one tool simultaneously, the tools can only be oriented straight out and parallel to one another, which prohibits truly collaborative work between the tools. Surgeons can greatly benefit from the increased precision, dexterity, and vision that robotic surgery systems offer, but such conventional systems are limited in their manipulability.

Another problem with conventional surgical robots is that parallel tube configurations extending from endoscopic devices do not provide triangulation of the tools in a workspace in the field of view near the tip of the endoscope. Additionally, such conventional configurations include tubes that extend generally parallel along a longitudinal axis, which makes it nearly impossible to apply off-axis forces for pushing or pulling tissue from side to side. Such configurations place also place a nominal interaction point where first and second tools interact significantly beyond the field of view and effective workspace at the tip of the endoscope. As such, it is difficult to manipulate tissue using two endoscopic tools working together using conventional devices.

What is needed, then, are improvements in devices and methods for performing robotic surgery, and specifically for controlling and manipulating first and second tools in cooperation, in a field of view near the tip of an endoscopic device.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

A device for performing minimally invasive surgery includes a concentric tube assembly with a distal tip configured for insertion into a patient's body through a small incision or orifice. The tube assembly includes a channel and a guide tube housed within the channel. The guide tube is configured to translate axially and to rotate relative to the channel. An inner tube is positioned inside the guide tube and is also independently moveable in axial translation and rotation relative to the guide tube. The guide tube is operable to steer the distal end of the inner tube to a desired location in a tissue workspace defined at the end of the tube assembly.

The guide tube includes a pre-shaped, highly-curved distal end. The channel also has a curved shape near its distal opening. The curved channel and highly-curved guide tube work together to form an elbow-like configuration, allowing the guide tube to enter a tissue workspace at an angle relative to a centerline axis. Such an angled entry into the workspace provides superior triangulation and manipulation of tissue.

In some embodiments, the present disclosure provides an apparatus for performing surgery, comprising a surgical robot including an endoscopic device extending from the surgical robot, the endoscopic device including an outer sheath, an inner sheath and a channel disposed inside the inner sheath. A guide tube is positioned inside the channel, the guide tube including a proximal end extending toward the surgical robot and a highly-curved distal end extending away from the surgical instrument. An inner tube is housed inside the guide tube, wherein the inner tube is axially moveable and rotatable relative to the guide tube. The highly-curved distal end of the guide tube includes a curvature between about 50 m^(−1) and about 100 m^(−1).

In further embodiments, the highly-curved distal end of the guide tube includes a curvature between about 50 m^(−1) and about 100 m^(−1).

In additional embodiments, the present disclosure provides an apparatus for performing surgery, comprising a surgical robot including an endoscopic device extending from the surgical robot, the endoscopic device including an outer sheath, an inner sheath and first and second channels disposed inside the inner sheath. A first guide tube is positioned inside the channel, the first guide tube including a proximal end extending toward the surgical robot and a first highly-curved distal end extending away from the surgical robot. A second guide tube is positioned inside the channel, the second guide tube including a proximal end extending toward the surgical robot and a second highly-curved distal end extending away from the surgical robot. A first inner tube is housed inside the first guide tube, wherein the first inner tube is axially moveable and rotatable relative to the first guide tube. A second inner tube is housed inside the second guide tube, wherein the second inner tube is axially moveable and rotatable relative to the second guide tube. The first highly-curved distal end of the first guide tube includes a curvature between about 50 m^(−1) and about 100 m^(−1), and the second highly-curved distal end of the second guide tube includes a curvature between about 50 m^(−1) and about 100 m^(−1).

In further embodiments, the first highly-curved distal end of the first guide tube includes a curvature of about 72 m^(−1), and the second highly-curved distal end of the second guide tube includes a curvature of about 72 m^(−1).

Another objective of the present disclosure is to provide a device and methods for effectively manipulating tissue using first and second tools in a field of view near the tip of an endoscopic device.

Numerous other objects, advantages and features of the present disclosure will be readily apparent to those of skill in the art upon a review of the following drawings and description of a preferred embodiment.

DETAILED DESCRIPTION

Figure 1:
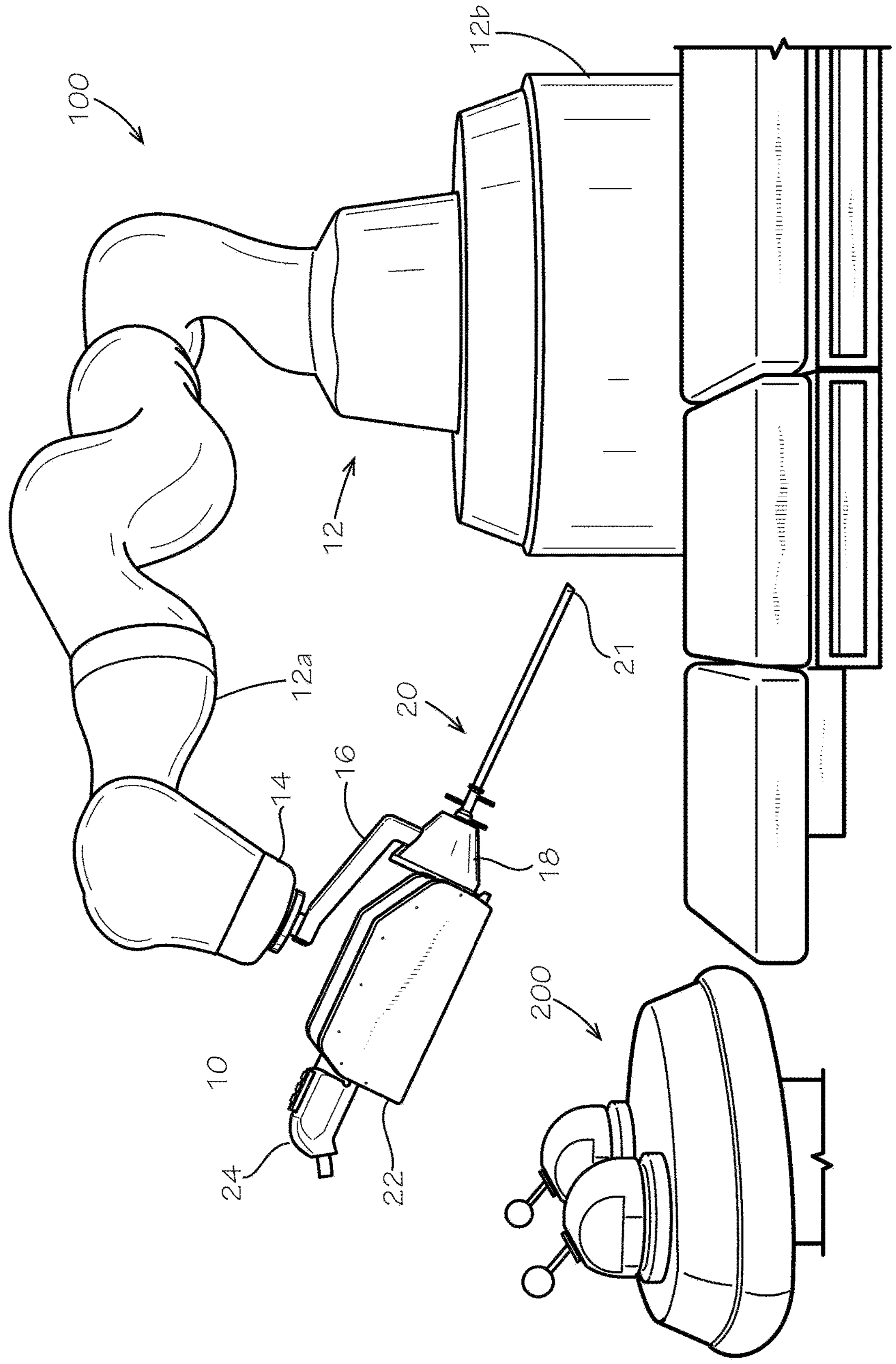
FIG. 1 is a side perspective view of an embodiment of a minimally invasive surgery apparatus in accordance with the present invention.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention. Those of ordinary skill in the art will recognize numerous equivalents to the specific apparatus and methods described herein. Such equivalents are considered to be within the scope of this invention and are covered by the claims.

In the drawings, not all reference numbers are included in each drawing, for the sake of clarity. In addition, positional terms such as “upper,” “lower,” “side,” “top,” “bottom,” etc. refer to the apparatus when in the orientation shown in the drawing. A person of skill in the art will recognize that the apparatus can assume different orientations when in use.

The present disclosure provides a minimally invasive surgery apparatus including a guide tube with a highly-curved distal end. The guide tube is housed in a longitudinal channel along the length of an endoscope or resectoscope type tube assembly. The channel many have a straight or a curved profile in various embodiments. The guide tube includes a highly-curved configuration that provides for superior triangulation in the workspace and manipulability for a surgeon to engage tissue near the distal end of an endoscope or resectoscope. The parameters of curvature at the distal end of the guide tube are optimized to provide enhanced performance.

The distal section of the guide tube is highly-curved and is configured for deployment into a tissue workspace beyond the distal tip of the endoscope inside a patient’s body. The distal section of the guide tube may be rotated and translated relative to the channel in which it is housed, and an inner tube including a surgical tool (such as an electrosurgery tool or cutting device) may be positioned inside the interior of the guide tube and extending out the distal end of the guide tube to access the tissue workspace within the field of view of a camera lens. The highly-curved distal end of the guide tube provides enhanced triangulation and dexterity in the workspace, and provides optimized performance for minimally invasive surgery.

As an example, an embodiment of a minimally invasive surgery apparatus 100 is shown generally in FIG. 1. The apparatus includes a surgical robot apparatus 10 mounted to a support 12. In some embodiments, support 12 includes a robotic arm **12*a* extending from a stationary base 12*b*. A mount 14 on the end of robotic arm 12***a* is configured for attachment to the surgical robot apparatus 10 via a brace 16 in some embodiments. Support 12 provides a programmable positioning device for precisely controlling the position and orientation of surgical robot apparatus 10 in three-dimensional space relative to a human or animal patient positioned on an operating table below the device.

An input console 200 is located remote from the support 12 and surgical robot apparatus 10. Input console 200 provides input to control one or more devices located on surgical robot apparatus 10.

Figure 2:
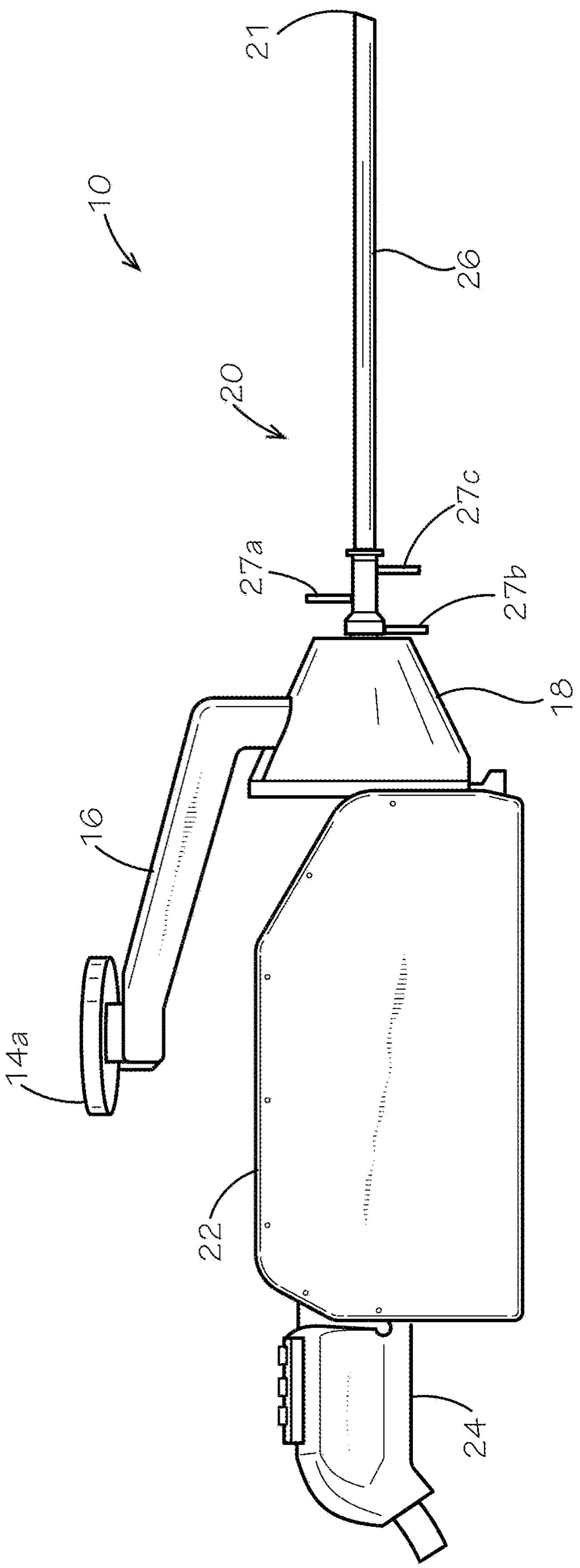
FIG. 2 is a detail side view of the minimally invasive surgery apparatus of FIG. 1.

Referring further to FIG. 1 and FIG. 2, surgical robot apparatus 10 includes an interface 18 connecting a rigid tube assembly 20 with instrument base 22. Tube assembly 20 includes a longitudinal endoscope or resectoscope type structure comprising an outer sheath 26 and a plurality of tubes housed inside the outer sheath 26. One or more ports 27*a*, 27*b*, 27*c* are coupled to the tube assembly 20 to provide irrigation, suction or other functions during a surgical operation. Tube assembly 20 includes a distal end 21 oriented away from instrument base 22 for insertion into the tissue of a patient. A camera 24 is positioned on base 22, including a lens passing through the tube assembly 20 toward the distal end 21 for providing visualization of a tissue workspace adjacent distal end 21 when the tube assembly 20 is inserted into a patient's body. Surgical robot apparatus 10 also includes an adapter 14*a* configured for attachment to mount 14, shown in FIG. 1.

Figure 3A:
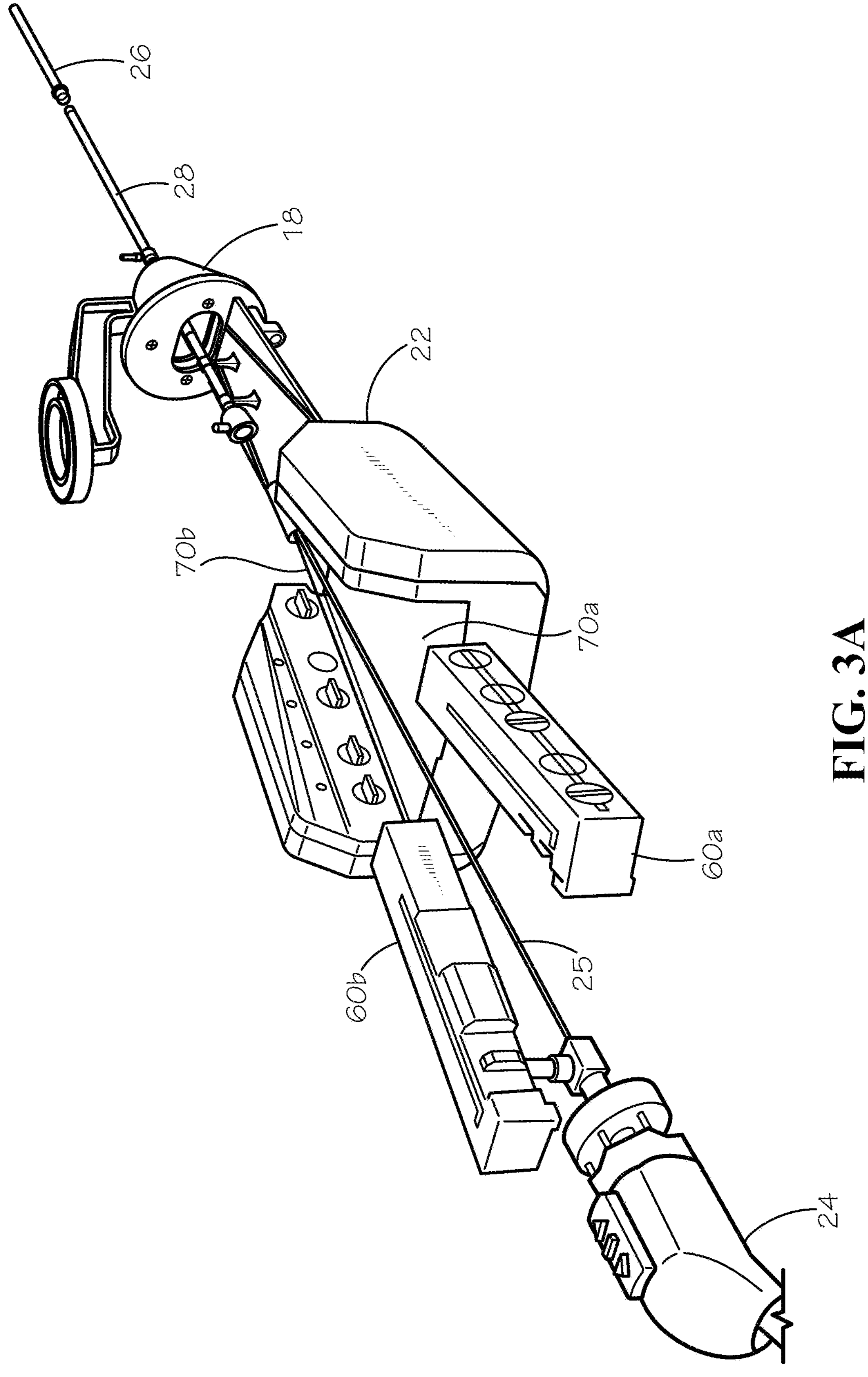
FIG. 3A is an exploded perspective view of an embodiment of the minimally invasive surgery apparatus of FIG. 1.

Referring to FIG. 3A, camera 24 is positioned on instrument base 22 to provide real-time imagery to a remote display for a surgeon to view during a surgical procedure. Camera 24 includes a rod-shaped lens 25 extending through a longitudinal lens passage 80 inside the tube assembly 20 such that the lens provides a field of view including the tissue workspace immediately beyond the distal tip of the tube assembly. In some embodiments, lens passage 80 includes a rigid tube extending along the inside of the tube assembly 20 to protect the lens 25 as it is housed within, inserted and/or removed from the device. Lens passage 80 includes a funnel-shaped insertion port at its proximal end in some embodiments.

Figure 3B:
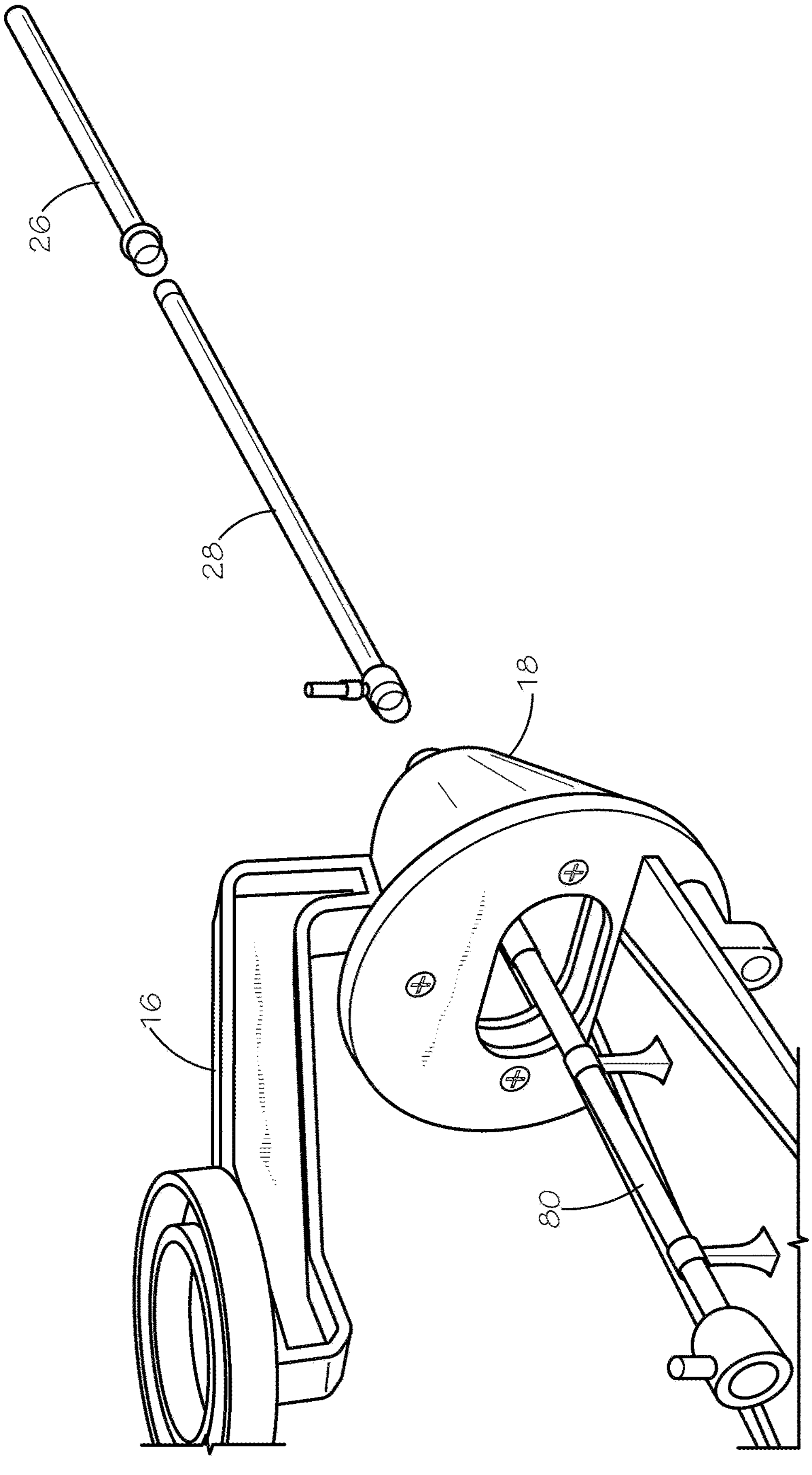
FIG. 3B is a detail exploded perspective view of an embodiment of the minimally invasive surgery apparatus of FIG. 1.

Referring further to FIGS. 3A and 3B, tube assembly 20 includes an outer sheath 26 and an inner sheath 28. An annular plenum is defined between the outer surface of the inner sheath 28 and the inner surface of the outer sheath 26 such that gas or fluid may be transported through the plenum during a surgical procedure.

Referring further to FIG. 3A, in some embodiments, surgical robot apparatus 10 includes a first tool cartridge 60*a* and a second tool cartridge 60*b*. Each tool cartridge is configured as a modular part that can be installed in the instrument base 22. Each tool cartridge includes a drive mechanism configured to manipulate a tube array coupled to the cartridge. For example, first tool cartridge 60*a* is coupled to the proximal end of a first tube array 70*a* such that first tube array 70*a* extends away from the first tool cartridge 60*a* toward interface 18. Similarly, second tool cartridge 60*b* is coupled to the proximal end of a second tube array 70*b* such that the second tube array 70*b* extends away from the second tool cartridge 60*b* toward interface 18. Each tool cartridge 60*a*, 60*b* may be interchangeable with other like tool cartridges on instrument base 22. In some embodiments, each tool cartridge is disposable.

Figure 4:
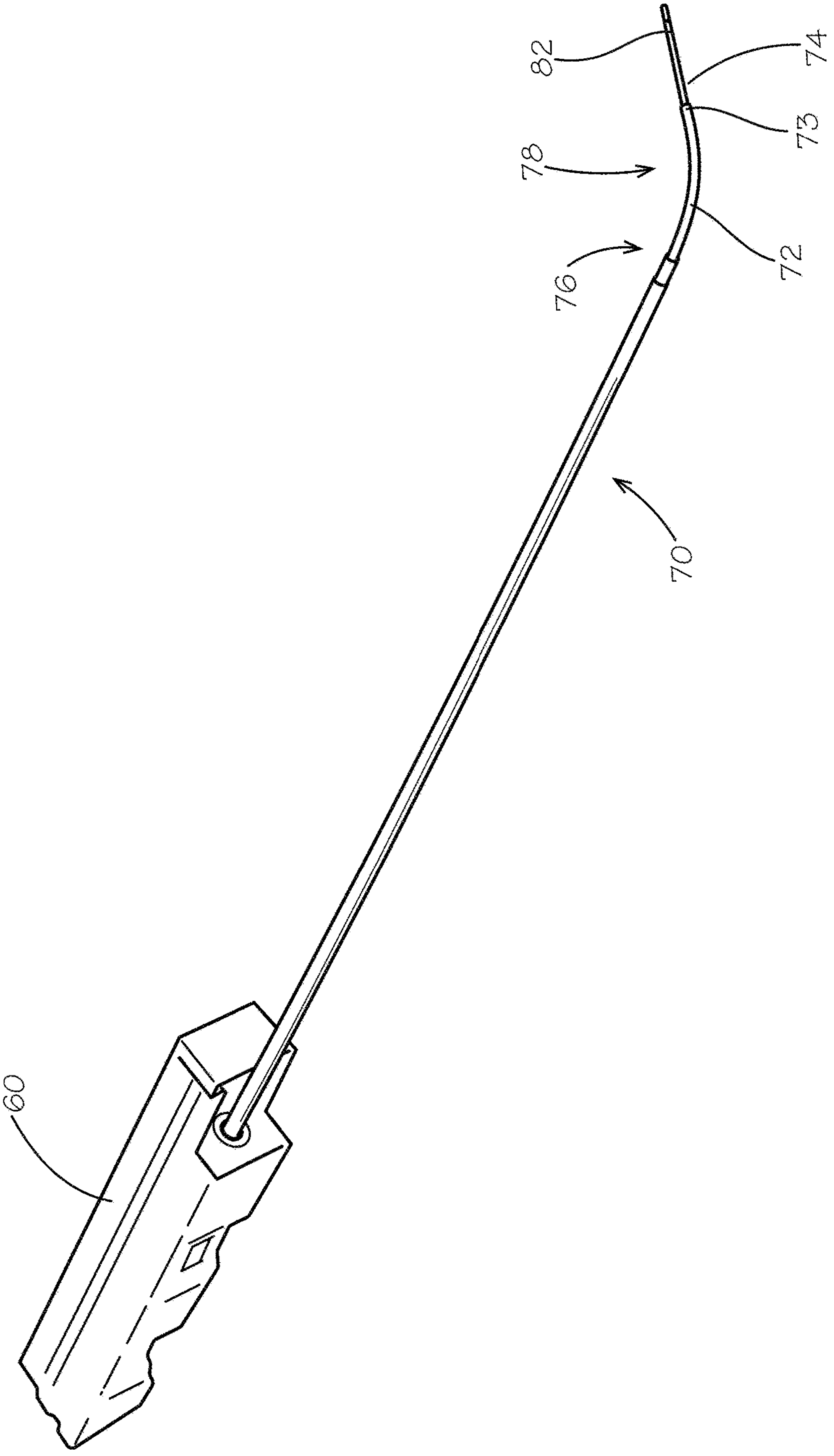
FIG. 4 is a perspective view of an embodiment of a tool cartridge apparatus for a minimally invasive surgery apparatus.

An embodiment of a tool cartridge 60 with an associated tube array 70 is shown in FIG. 4. Tool cartridge 60 includes a housing joined to the proximal end of the tube array 70. Tube array 70 includes a concentric tube array comprising a guide tube, or outer tube, 72 and an inner tube 74 positioned inside the guide tube 72. Guide tube 72 has a highly-curved distal end 78, and the inner tube 74 protrudes out of the distal tip 73 of the guide tube 72. Inner tube 74 includes a surgical tool 82 such as an electrosurgery tip, a cutting tool or a tissue manipulator protruding from its distal end in some embodiments. During a surgical procedure, inner tube 74 may be translated axially or rotated about its longitudinal axis independently of the guide tube 72. Highly-curved guide tube 72 steers the inner tube 74 to a desired location in the tissue workspace. Inner tube 74 is coupled to one or more internal drive components inside tool cartridge 60 to provide independent axial translation and rotation controls in some embodiments.

During use, guide tube 72 may also be translated and rotated by independent drive components inside tool cartridge 60. As such, due to the curved portion 78 of the guide tube 72, a range of motion may be achieved by rotating and translating guide tube 72 and inner tube 74 using independent drive components in tool cartridge 60.

Figure 5:
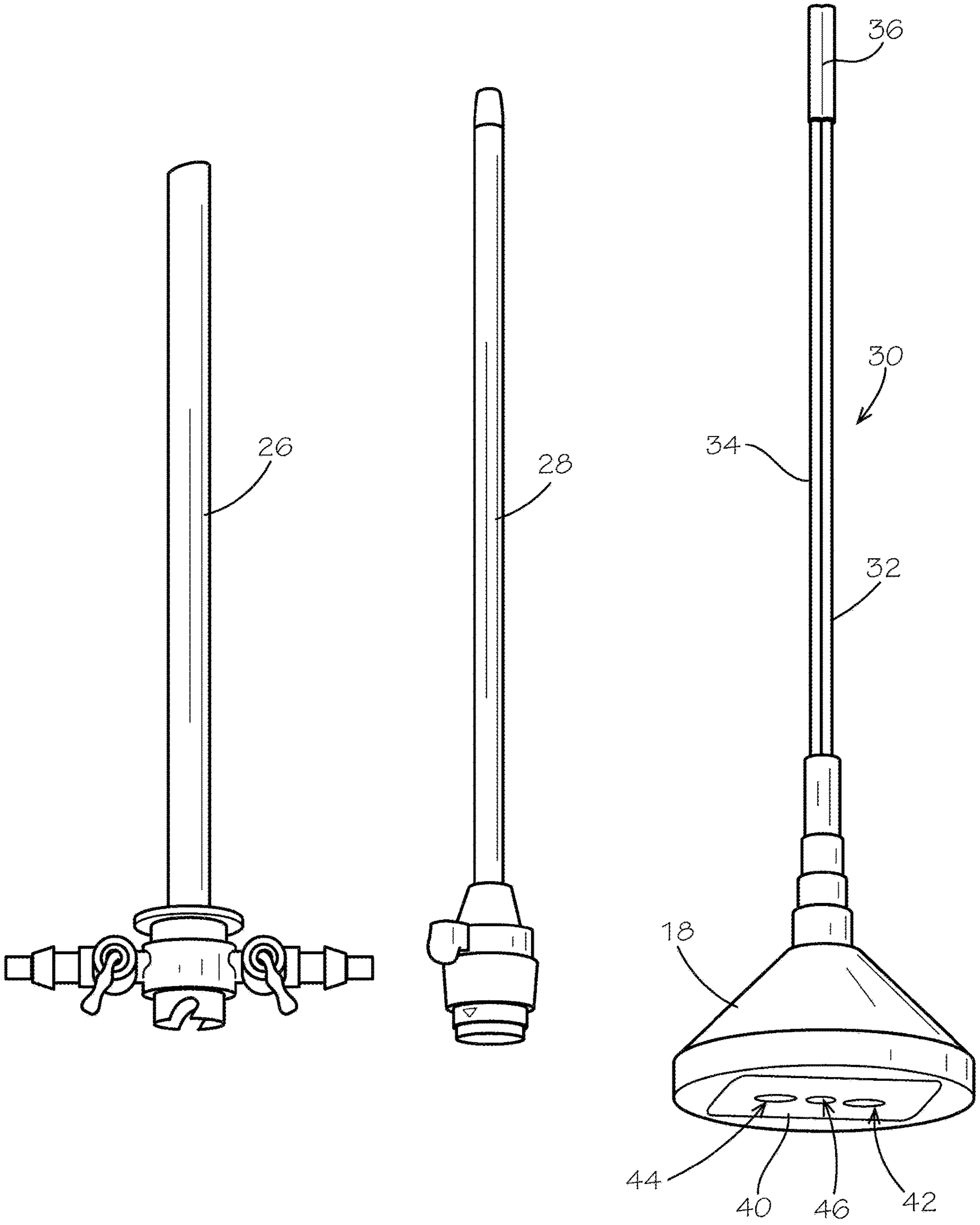
FIG. 5 is an exploded top view of an embodiment of a tube assembly of a minimally invasive surgery apparatus including an outer sheath, an inner sheath and a sheath insert including first and second channels.

The tube array 70 is housed inside a longitudinal channel assembly, or sheath insert 30, on the interior of an endoscope or resectoscope type device in some embodiments. As shown in FIG. 5, a sheath insert 30 includes a first channel 32 for housing a first concentric tube array 70*a* and a second substantially parallel channel 34 for housing a second concentric tube array 70*b*. Sheath insert 30 is positioned axially inside the endoscope or resectoscope inner sheath 28 to provide interior channels for housing a one or more concentric tube arrays. When assembled, first and second channels 32, 34 are positioned inside the inner sheath 28, and the outer sheath 26 is positioned on the exterior of the inner sheath 28. In some embodiments, first and second channels 32, 34 each include a hollow interior space forming a substantially round cross-sectional profile dimensioned such that each concentric tube array 70*a*, 70*b* will fit closely inside while allowing each guide tube 72, 172 to be rotated and axially translated independently inside its corresponding channel.

Figure 6:
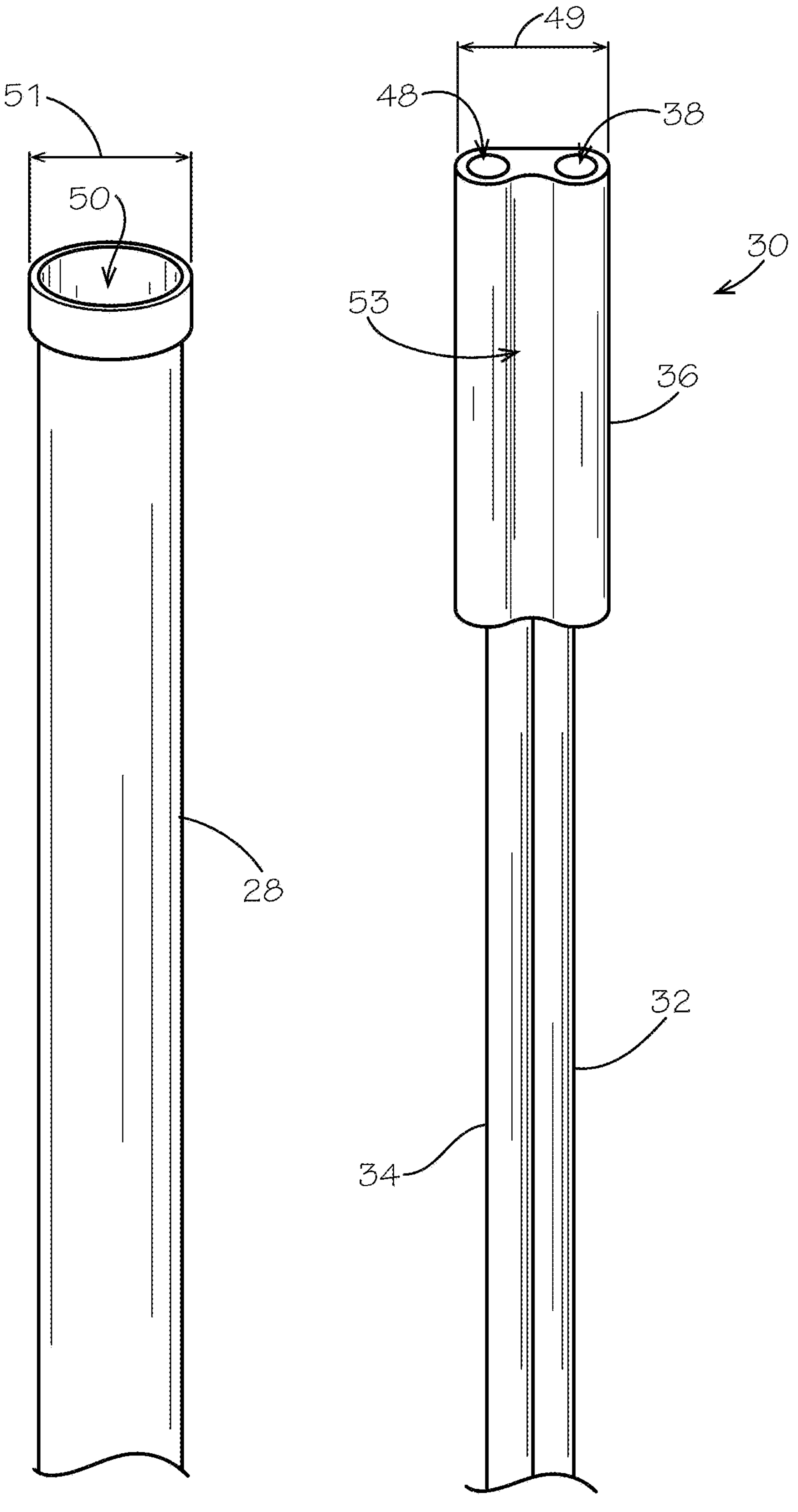
FIG. 6 is a partial cross-sectional view of an embodiment of a channel insert configured for positioning inside a sheath.

Referring to FIG. 6, an embodiment of a distal end of a sheath insert 30 is shown alongside an inner sheath on an endoscope or resectoscope. Sheath insert 30 includes a first channel 32 and a second channel 34. First and second channels 32, 34 diverge at the distal end. First channel 32 terminates at a first channel opening 38, and second channel 34 terminates at a second channel opening 48. A channel bushing 36 is disposed on the distal ends of first and second channels 32, 34 at the distal end of the sheath insert 30. Channel bushing 36 surrounds the distal ends of first and second channels 32, 34 in some embodiments. Channel bushing 36 provides support to the first and second channels 32, 34 in the region of divergence. Channel bushing 36 also interfaces with the interior wall of inner sheath 28 to properly align first and second channels 32, 34 at the desired location on the distal opening 50 of inner sheath 28. In some embodiments, channel bushing 36 includes a channel bushing width 49 substantially equal to the inner diameter 51 of inner sheath 28 at its distal opening 50. Channel bushing 36 comprises a polymer material in some embodiments. As shown in FIG. 6, a lens groove 53 provides a recess in channel bushing 36 shaped to accommodate the rod lens coupled to the camera. Channel bushing 36 and first and second channels 32, 34 are joined such that the entire assembly may be inserted axially into inner sheath 28, or may be pulled axially from inner sheath 28, following use. Sheath insert 30 is disposable in some embodiments. In other embodiments, sheath insert 30 is interchangeable with other like sheath inserts. For example, for a particular procedure, it may be desirable to use first and second channels 32, 34 having certain characteristics, such as inner diameter, channel shape or curvature at the distal end. However, for other procedures, it may be desirable to use first and second channels 32, 34 with different characteristics. Thus, using the system and methods of the present disclosure, a user may swap sheath inserts 30 having different characteristics for different operations.

Figure 7:
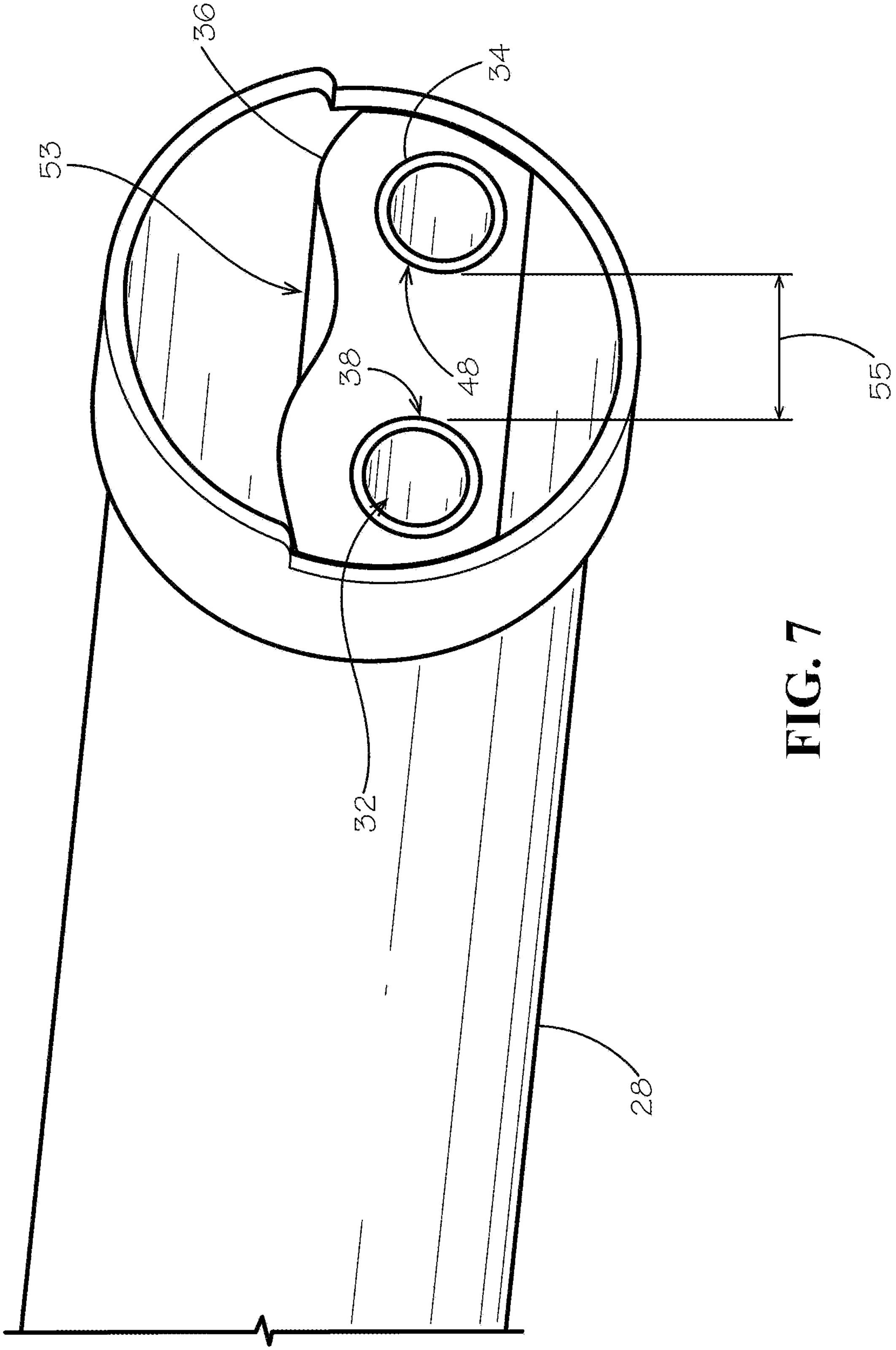
FIG. 7 is a perspective view of an embodiment of the distal end of an inner sheath including first and second channel openings and a channel bushing.

Referring to FIG. 7, an embodiment of a sheath insert 28 including first and second channels 32, 34 is shown. First channel 32 opens at a first channel distal opening 38, and second channel 34 opens at a second channel distal opening 48. First and second channel distal openings 38, 48 are separated by a channel spacing 55. In some embodiments, channel spacing 55 is greater than the inner diameter of first or second channel 32, 34. In some embodiments, channel spacing 55 is greater than about twice the inner diameter of first channel 32 or second channel 34. First and second channel distal openings 38, 48 are spaced because both first and second channels 32, 34 diverge away from the axial centerline of inner sheath 28 in a curved orientation. As shown in FIG. 7, a lens may be positioned in the lens groove 53 inside inner sheath 28 above the channel bushing 38.

Referring again to FIG. 5 and FIGS. 8 and 9, in some embodiments, a sheath insert 30 includes an interface 18 providing a rigid funnel-shaped structure connected at one end to the first and second channels 32, 34 and open at the other end for insertion of the tube arrays 70*a*, 70*b* and the rod lens 25 from camera 24. For example, in some embodiments, a steering plug 40 is positioned in interface 18. Steering plug 40 defines a first port 42 shaped to receive longitudinal insertion of first tube array 70*a* (coupled to first cartridge 60*a* in some embodiments), and a second port 44 shaped to receive longitudinal insertion of second tube array 70*b* (coupled to second cartridge 60*b* in some embodiments). Steering plug 40 also defines a lens insertion port 46 positioned to receive longitudinal insertion of a rod lens 25 in some embodiments.

Figure 8:
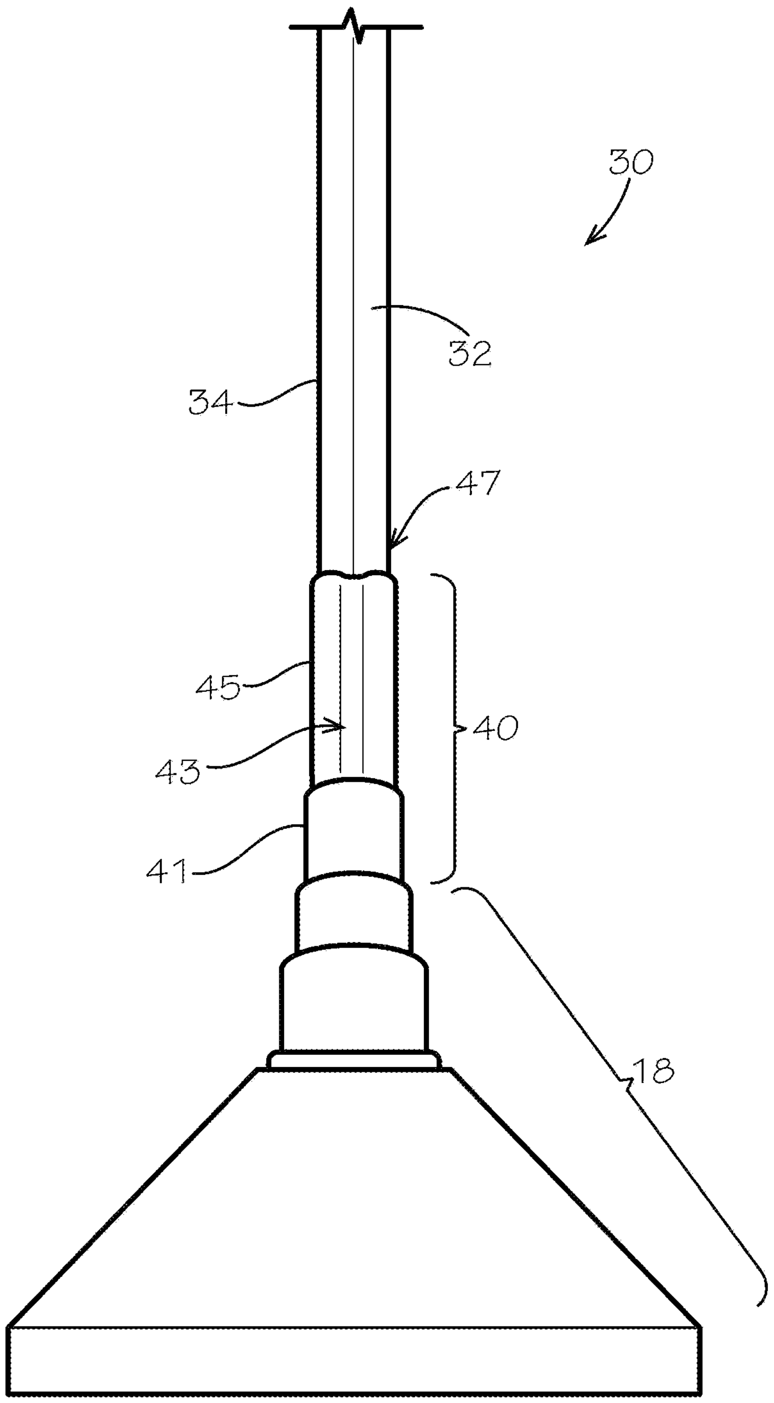
FIG. 8 is a perspective view of an embodiment of a sheath insert including first and second channels.

Steering plug 40, as shown in FIG. 8, includes a sheath adapter 45 surrounding the proximal ends of first and second channels 32, 34. Sheath adapter 45 is similar in shape and function to channel bushing 36 in some embodiments. Sheath adapter 45 includes an outer diameter near the inner diameter of inner sheath 28, such that sheath adapter 45 fits closely along the interior wall of inner sheath 28 when received in the inner sheath 28. A lens guide 43 is defined on the sheath adapter, forming a groove to receive a portion of a lens passing longitudinally along the interior length of the inner sheath 28. An insert bushing 41 forms a rigid cylinder at the proximal end of the sheath adapter 45, configured for engagement with the inner sheath 28. In some embodiments, insert bushing 41 forms a seal around the interior of the inner sheath 28 on the endoscope or resectoscope.

Figure 9:
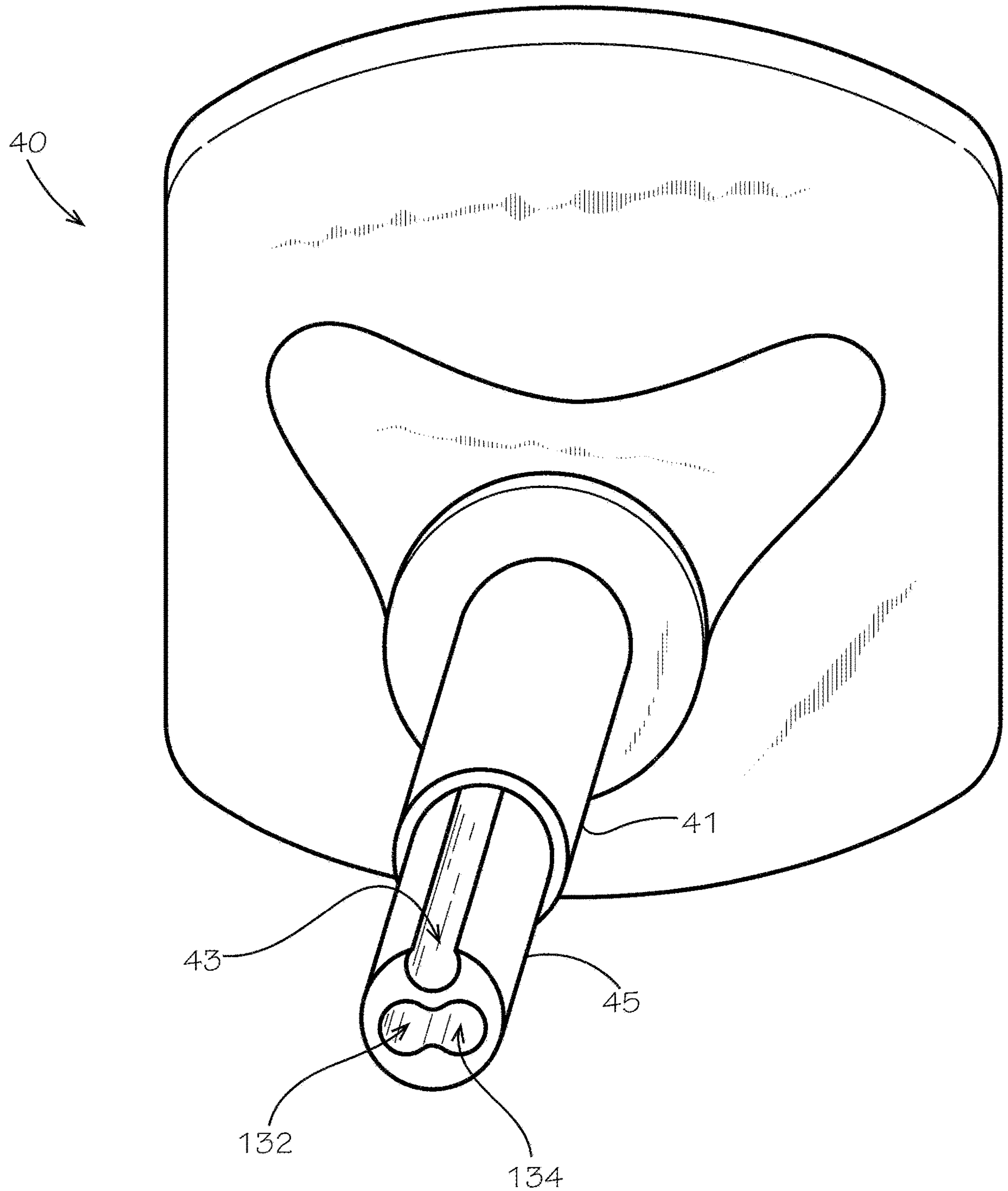
FIG. 9 is a perspective view of an embodiment of a steering plug for use on a sheath insert.

As shown in FIG. 9, steering plug 40 may be formed as a unitary piece of a non-metal material, such as a polymer material. Steering plug 40 may be removed from interface 18 and replaced. In some embodiments, steering plug 40 is disposable. Steering plug 40 may be held in place inside interface 18 using a friction fit in some embodiments. Steering plug 40 may also fit closely inside the internal contours of interface 18 to form a seal between interface 18 and the steering plug 40 in some embodiments.

Figure 10:
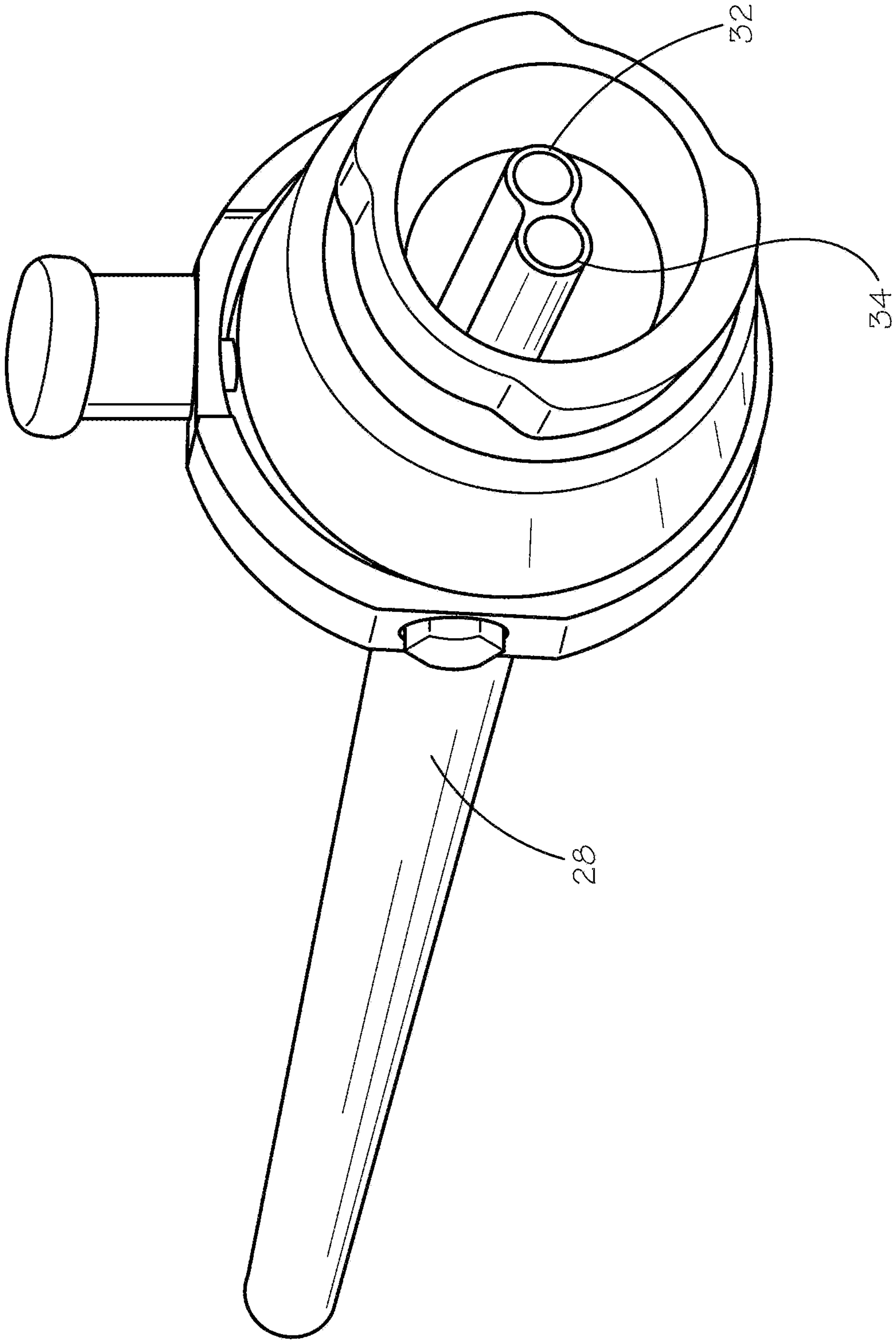
FIG. 10 is a perspective view of an embodiment of an inner sheath with first and second channels housed therein.

Steering plug 40 includes a first socket 132 shaped to receive the proximal end of first channel 32, and a second socket 134 shaped to receive the proximal end of second channel 34. Lens guide 43 defines a hollow passage in sheath adapter 45 shaped to receive passage of a lens, such as a fiber optic lens passing through the steering plug toward the distal end of the endoscope or resectoscope. As seen in FIG. 10, the proximal end of first channel 32 may fit closely inside first socket 132, shown in FIG. 9, and similarly, the proximal end of second channel 34 may fit closely inside second socket 134. Thus, first and second channels 32, 34 may be in open communication with first port 42 and second port 44, respectively, shown in FIG. 5. A first tube array including a guide tube 72 and an inner tube 74 may be positioned into first port 42, through steering adapter 40, and into first channel 32. Similarly, a second tube array including a second guide tube 172 and a second inner tube 174 may be positioned into second port 44, through steering adapter 40, and into second channel 34.

Figure 11:
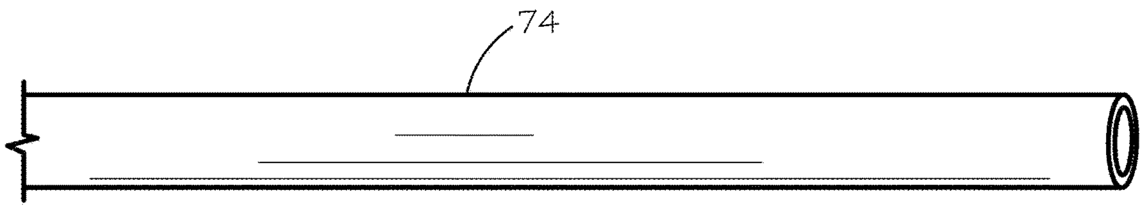
FIG. 11 is side view of an embodiment of an inner tube.
Figure 12:
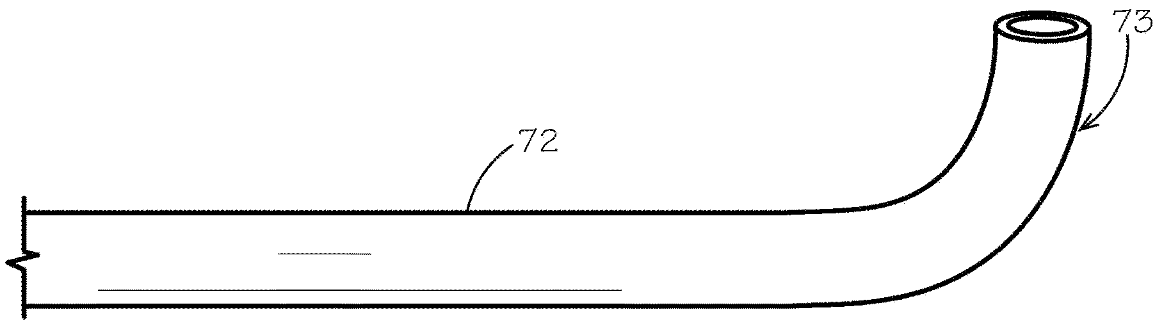
FIG. 12 is a side view of an embodiment of a highly-curved guide tube.
Figure 13:
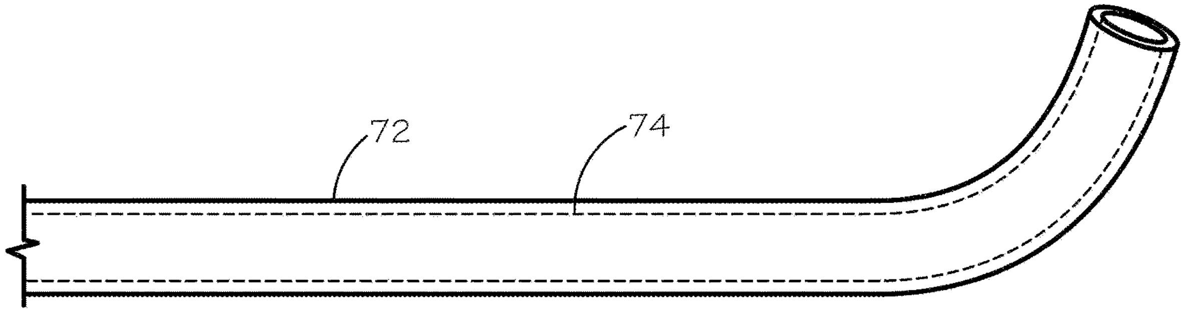
FIG. 13 is a side view of an embodiment of a combined inner tube and highly-curved guide tube.

Referring to FIGS. 11-13, the present disclosure provides a tube array including a substantially straight inner tube 74 positioned inside a guide tube 72 with a highly-curved distal end 73. Inner tube 74 includes a surgical tool positioned on its distal tip in some embodiments. Inner tube 74 is substantially straight along its length, although in some embodiments it may attain a slight curvature due to its use in a curved channel and/or in a curved guide tube. Because inner tube 74 is housed inside a guide tube 72 having a highly-curved end, inner tube 74 may gain some curvature during use by being slightly strained by the curved guide tube in which it is housed. In some embodiments, inner tube 74 has a distal end that attains a curvature less than about 10 m^(−1), having a radius greater than about 100 mm. In some embodiments, inner tube 74 includes a portion with a radius of between about 100 mm and about 500 mm.

Referring to FIG. 12, guide tube, or outer tube 72, includes a highly-curved distal end 73. Guide tube 72 comprises nitinol in some embodiments, and the curvature of the highly-curved distal end 73 of guide tube 72 is shapeset to a desired curvature to provide optimized performance. In some embodiments, the curvature of highly-curved distal end 73 of guide tube 72 is shapeset to a curvature between about 50 m^(−1) and about 100 m^(−1). In further embodiments, highly-curved distal end 73 of guide tube 72 is shapeset to a curvature between about 60 m^(−1) and about 80 m^(−1). In further embodiments, highly-curved distal end 73 of guide tube 72 is shapeset to a curvature of about 72 m^(−1) to provide optimized performance and manipulability in the workspace.

Referring further to FIG. 13, when inner tube 74 is positioned inside guide tube 72, the less-curved configuration of inner tube 74 slightly straightens distal end 73 of guide tube 72, further reducing the curvature of the distal end 73 of guide tube 72 to a curvature between about 60 m^(−1) and about 65 m^(−1). In further embodiments, the combined inner tube 74 and guide tube 72 includes a distal tip 73 with a combined effective curvature of about 63 m^(−1). In further embodiments, the present disclosure includes a tube array comprising a guide tube 72 and an inner tube 74 housed inside the guide tube 72, wherein tube array includes a combined curved distal tip with a combined effective curvature of greater than about 40 m^(−1) and less than about 100 m^(−1). In some embodiments, these parameters apply to both first guide tube 72 and first inner tube 74 housed inside first channel 32 and also second guide tube 172 and second inner tube 174 housed inside second channel 34.

Figure 14:
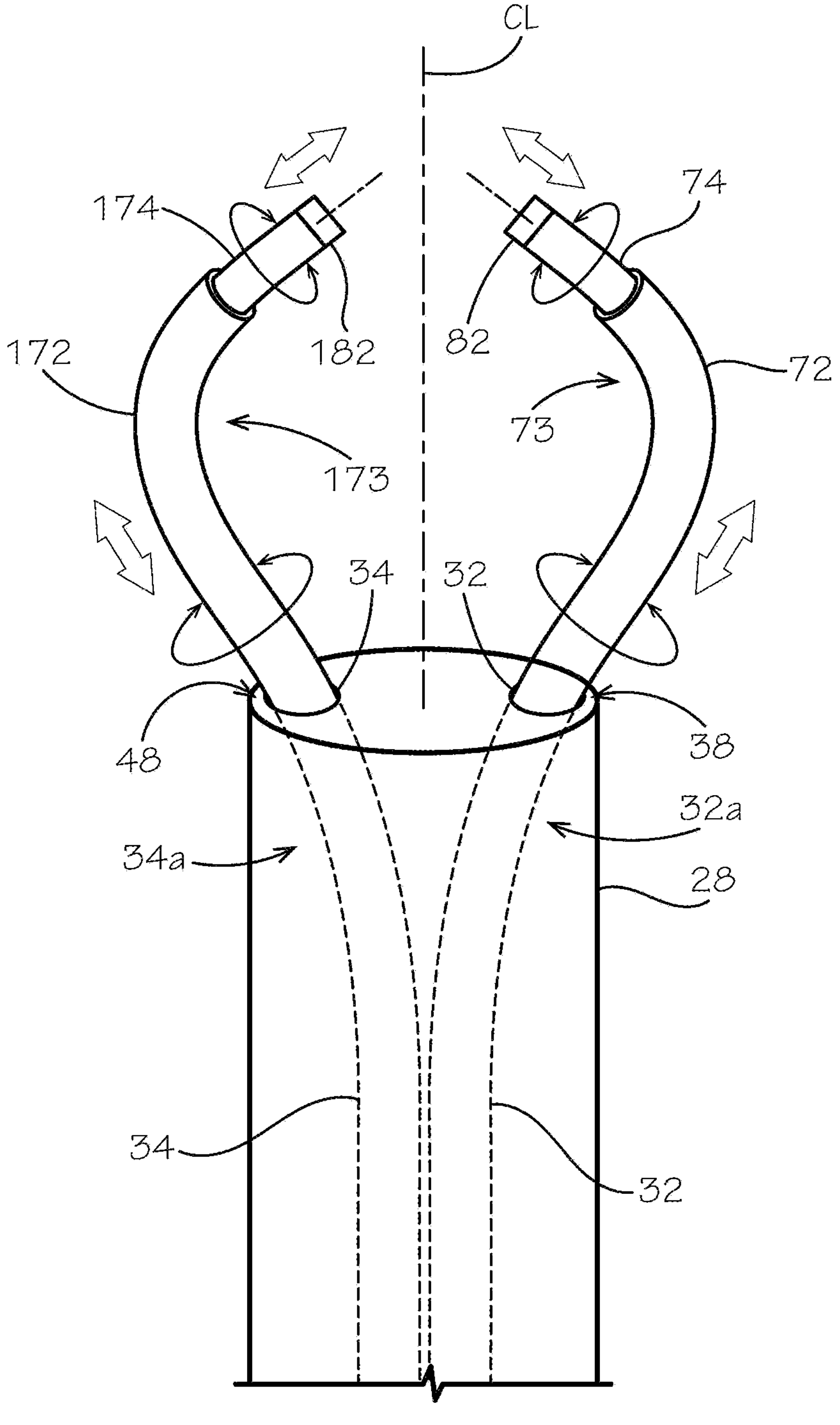
FIG. 14 is a perspective view of an embodiment of a surgical robot apparatus including first and second highly-curved guide tubes and first and second inner tubes extending therefrom.

Referring to FIG. 14, in some embodiments first and second guide tubes 72, 172 are both curved as set forth above. By providing first and second guide tubes 72, 172 each having a highly-curved distal end 73, 173, the curved ends may both extend simultaneously from the end of each respective channel 32, 34 at the end of an endoscope or resectoscope. The curvature of the first and second guide tubes 72, 172 moves the operational workspace of the tools closer to the tip of the endoscope and into the field of view. Additionally, the highly-curved distal ends of first and second guide tubes, along with the diverging curvatures of the first and second channels 32, 34, provide enhanced triangulation in the workspace. This allows the first and second inner tubes 74, 174 and corresponding first and second surgical tools 82, 182 to approach the centerline axis CL at a greater approach angle as compared to conventional surgical devices with lesser curvatures in the guide tubes 72 172 and channels 32, 34. In this configuration, first and second inner tubes 74, 174 may approach the workspace at greater triangulation angles and apply off-axis force vectors to better manipulate tissue in the workspace.

Some prior conventional devices include a guide tube with a curved distal end of about 3% strain. Such embodiments would not be considered highly-curved and would not be capable of the triangulation advantages of the present disclosure. In some embodiments, the present disclosure provides a first guide tube 72 and a second guide tube 172 each with a highly-curved distal end 73, 173 having strain greater than about 5%, forming an elbow-shaped configuration that provides an improved triangulation orientation for performing surgery, as shown in FIG. 14. In some embodiments, each guide tube 72, 172 includes a highly-curved distal end 73, 173 with a strain of about 8%. In further embodiments, each guide tube 72, 172 includes a highly-curved distal end with a strain between about 8% and about 10%.

Inner tubes 74, 174 are provided with a lower curvature geometry in some embodiments to provide a natural feeling to a surgeon, due to common surgical tools having a reduced curvature, or substantially straight, orientation. For example, surgeons trained on laparoscopic equipment are used to having tools that translate axially into the workspace. For this reason, adapting surgical robots using endoscopic tools to have axial translation at the distal tip of the tool provides an intuitive approach for surgeons. As such, by providing inner tubes 74, 174 with a lesser curvature than the guide tube, that can be retracted or extended out the distal tip opening of guide tube 72, the present disclosure provides a system with an intuitive configuration for manipulating tissue using a tool on the distal tip of the inner tube 74 in a field of view of an endoscope or resectoscope.

Referring further to FIG. 14, although guide tubes with highly-curved distal ends provide enhanced operability, additional benefits are realized by providing first and second channels 32, 34 with curved, diverging distal ends 32*a*, 34*a* curving away from a centerline CL of the endoscope or resectoscope. For example, as shown in FIG. 14, first channel 32 extends longitudinally inside inner sheath 28, and first channel 32 includes a curved distal end 32*a* diverging away from the centerline CL. Similarly, second channel 34 extends longitudinally inside inner sheath 28 alongside first channel 32, and second channel 34 includes a curved distal end 34*a* diverging away from the centerline CL and away from first channel 32. First and second channels 32, 34 are tubes on sheath insert 30 in some embodiments. Each of first and second channel 32, 34 provide a passage for first and second guide tubes 72, 172, respectively. First guide tube 72 can translate axially and also rotate inside first channel 32, and second guide tube 172 can translate axially and also rotate inside second channel 34.

As shown in FIG. 14, by providing first and second channels 32, 34 with distal ends 32*a*, 34*a* curving away from each other and away from centerline CL, the highly-curved distal ends 73, 173 on guide tubes 72, 172 are able to extend away from the centerline CL at an angle when extended from the first and second distal end openings 38, 48 of each channel. In some embodiments, first and second channels 32, 34 include a curvature between about 15 m^(−1) and about 30 m^(−1). Such curvature ranges provide first and second channels 32, 34 each angled away from centerline CL at an angle of about 10 to 15 degrees. As such, the ranges of motion of first and second highly-curved guide tubes 72, 172 extending initially away from centerline CL due to curved channels 32, 34, and then back toward centerline CL following extension, provides superior triangulation in the workspace adjacent the end of the endoscope or resectoscope. Such a configuration also moves the nominal interaction point to a better position closer to the endoscope as opposed to similar configurations with straight channels.

Figure 15:
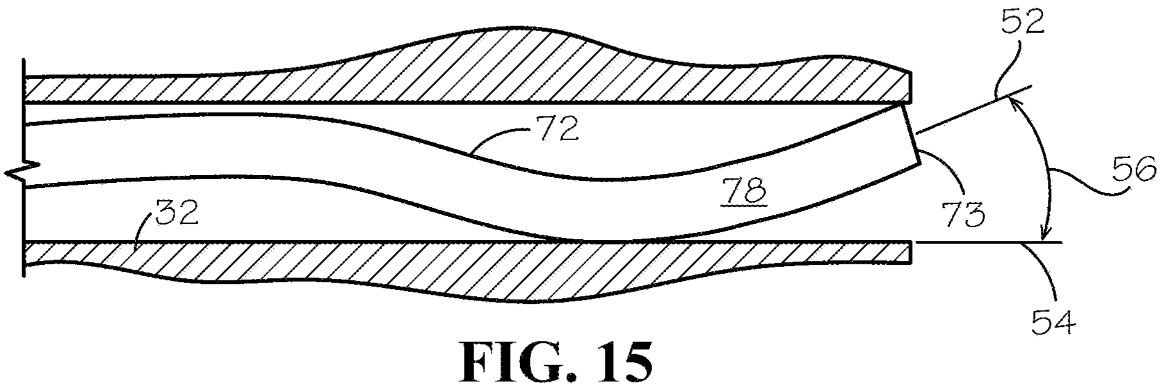
FIG. 15 is a partial cross-sectional view of an embodiment of a highly-curved guide tube inside a channel in a retracted position.

Referring to FIG. 15, in some embodiments when guide tube 72 is fully retracted in channel 32, the curvature of the highly-curved region 78 of guide tube 72 is constrained by the inner diameter of channel 32. From this position, the orientation of the distal end 73 of guide tube 72 projects along a linear extension axis 52 along which inner tube will travel if extended relative to guide tube 72. Due to the curvature of the guide tube 72 being constrained in the channel 32, a small volume of space 56 defined by the space between extension axis 52 and reference longitudinal axis 54 may be rendered inaccessible in the workspace region adjacent to the distal end of the endoscope.

Figure 16:
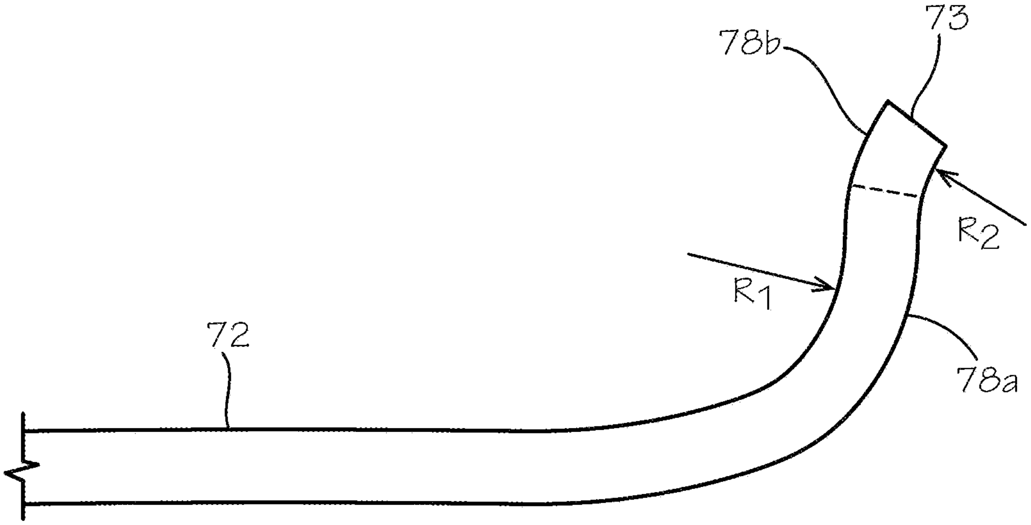
FIG. 16 is a side view of an embodiment of a guide tube with a double-curve configuration.

Referring to FIG. 16, to overcome this problem, in some embodiments, guide tube 72 includes a reverse curve, or double-curvature, configuration including a first curved region 78*a* and a second curved region 78*b*. First curved region 78*a* includes a first radius of curvature R1, and second curved region 78*b* includes a second radius of curvature R2. R1 and R2 are the same in some embodiments. Alternatively, R1 and R2 are different in other embodiments. First and second curved regions 78*a*, 78*b*, are curved in the same plane in some embodiments. First curved region 78*a* includes a first arc length, and second curved region 78*b* includes a second arc length less than the first arc length.

Figure 17:
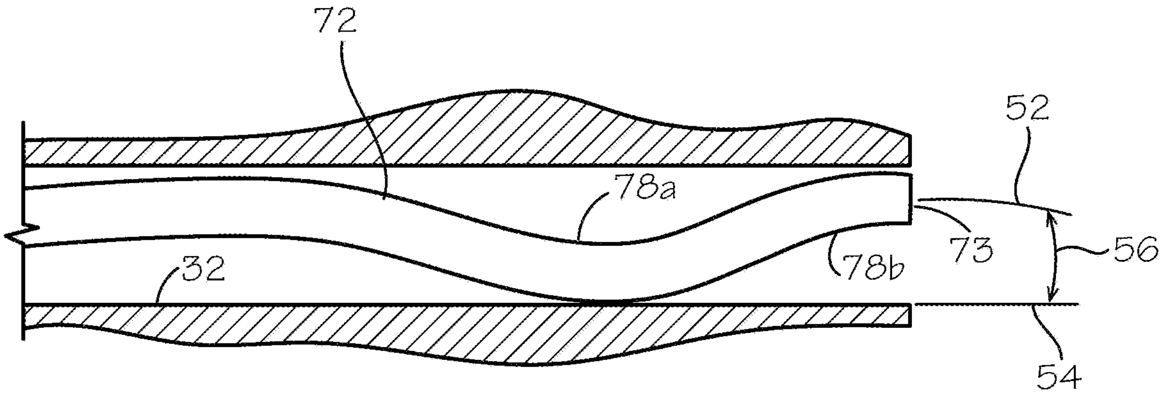
FIG. 17 is a partial cross-sectional view of an embodiment of a guide tube with a double-curve configuration positioned inside a channel in a retracted position.

Referring to FIG. 17, a guide tube 72 including a double-curvature configuration defines an extension axis 52 angled toward reference longitudinal axis 54. As such, the second curved region 78*b* orients the inner tube toward the centerline when the guide tube 72 is fully retracted in channel 32. Such a configuration reduces the size of the space 56 rendered inaccessible to the inner tube 74 when extended along the extension axis 52.

In some embodiments, the second curved region 78*b* includes less than about 10.0 mm of the end of the guide tube 72. In further embodiments, the second curved region 78*b* includes a curvature of about 40 m^(−1) to provide an improved range of motion. In further embodiments, the second curved region 78*b* includes about 5.0 mm at the end of the guide tube 72, and includes a curvature of between about 35 m^(−1) and about 45 m^(−1). In some embodiments, the first curved region has a curvature of between about 50 m^(−1) and about 100 m^(−1). In further embodiments, the first curved region has a curvature of about 72 m^(−1), and second curved region has a curvature of about 40 m^(−1).

In further embodiments, the disclosure provides first and second guide tubes, each guide tube including a double-curvature configuration. In some embodiments, the first curved region of each guide tube includes a shape-set curvature between about 70 m^(−1) and about 75 m^(−1). The second curved region of each guide tube includes a shape-set curvature of about 40 m^(−1) along the last five millimeters of each guide tube.

Figure 18:
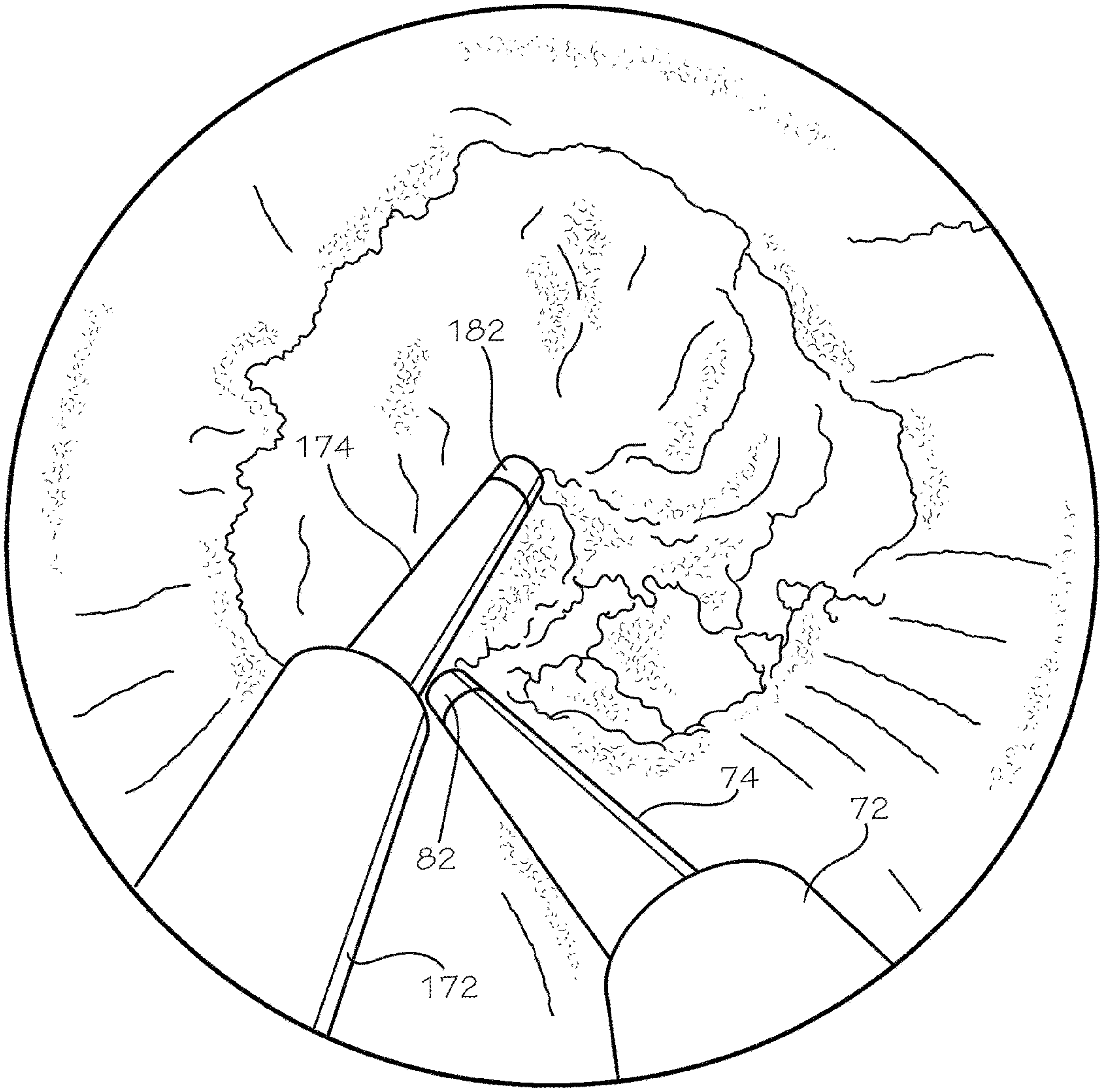
FIG. 18 is a perspective view of an embodiment of a field of view of a tissue workspace including first and second guide tubes and first and second inner tubes extending therefrom.

Referring to FIG. 18, a field of view at the distal end of an endoscope as seen by a surgeon during a procedure is illustrated. The field of view includes a first highly-curved guide tube 72 and a first inner tube 74 extending therefrom. A second highly-curved guide tube 172 is also shown, including a second inner tube 174 extending therefrom. A first surgical tool 82 is disposed on the first inner tube 74, and a second surgical tool 182 is disposed on the second inner tube 174. First and second inner tubes 74, 174 may be axially translated and rotated relative to each respective guide tube 72, 172, and first and second inner tubes 74, 174 work cooperatively to manipulate tissue.

In further embodiments, the present invention provides a method of performing minimally invasive surgery. The method includes providing a surgical instrument including a base and a tube assembly. The tube assembly includes a channel and a guide tube disposed in the channel, wherein the guide tube is axially moveable and rotatable inside the channel. The guide tube includes a proximal section and a highly-curved distal section positioned away from the base. An inner tube can be housed inside the guide tube from the base to the distal tip of the tube assembly. The method further includes a step of rotating the proximal section of the guide tube to cause a corresponding rotation of the distal end of the guide tube; translating the guide tube to a desired location in a tissue workspace; translating the inner tube through the highly-curved guide tube until the distal end of the inner tube is guided to a desired location in the tissue workspace by the guide tube; and performing a surgical procedure using the surgical tool.

Thus, although there have been described particular embodiments of the present invention of a new and useful CONCENTRIC TUBE APPARATUS FOR MINIMALLY INVASIVE SURGERY, it is not intended that such references be construed as limitations upon the scope of this invention.

What is claimed is:

1. An apparatus for performing surgery, comprising:

a surgical robot including an endoscopic device extending from the surgical robot, the endoscopic device including an outer sheath, an inner sheath and a channel disposed inside the inner sheath;

a guide tube positioned inside the channel, the guide tube including a proximal end extending toward the surgical robot and a highly-curved distal end extending away from the surgical robot;

an inner tube housed inside the guide tube, wherein the inner tube is axially moveable and rotatable relative to the guide tube, a surgical tool disposed in the inner tube, the surgical tool protruding from a distal end of the inner tube; and a tool cartridge, wherein the tool cartridge controls axial movement and rotation of the guide tube, wherein the tool cartridge controls axial movement and rotation of the inner tube independent of the control of the axial movement and rotation of the guide tube, and wherein the highly-curved distal end of the guide tube includes a shapeset curvature between about 50 m^(−1) and about 100 m^(−1), wherein a curvature of the inner tube is less than the shapeset curvature of the highly-curved distal end of the guide tube and less than a curvature of the channel, wherein the inner tube straightens the guide tube towards a longitudinal axis of the inner tube, forming a combined effective curvature of the combination of the quide tube and the inner tube, and wherein the combined effective curvature is greater than about 40 m^(−1).

2. The apparatus of claim 1, wherein the shapeset curvature of the highly-curved distal end of the guide tube is between about 70 m^(−1) and about 75 m^(−1).

3. The apparatus of claim 1, wherein the shapeset curvature of the highly-curved distal end of the guide tube is about 72 m^(−1).

4. The apparatus of claim 1, wherein the combined effective curvature is between 60 m^(−1) and about 65 m^(−1).

5. The apparatus of claim 1, wherein the combined effective curvature is greater than about 63 m^(−1).

6. The apparatus of claim 1, wherein the guide tube includes a first curved region and a second curved region.

7. The apparatus of claim 6, wherein the first curved region and the second curved region are oriented opposite each other in substantially the same plane of curvature.

8. The apparatus of claim 7, wherein the first curved region includes a first arc length and the second curved region includes a second arc length less than the first arc length, and the second curved region includes a curvature between about 35 m^(−1) and about 45 m^(−1).

9. The apparatus of claim 1, wherein the highly-curved distal end of the guide tube comprises nitinol.

10. The apparatus of claim 1, wherein the channel disposed inside the inner sheath is curved.

11. The apparatus of claim 10, wherein the curvature of the channel is less than the curvature of the highly-curved distal end of the guide tube, and wherein the inner tube is curved.

12. The apparatus of claim 1, wherein the inner sheath is disposed in the outer sheath, wherein the endoscopic device further includes a sheath insert disposed in the inner sheath, and wherein the channel is disposed in the inner sheath.

13. An apparatus for performing surgery, comprising:

a surgical robot including an endoscopic device extending from the surgical robot, the endoscopic device including an outer sheath, an inner sheath and first and second channels disposed inside the inner sheath;

a first guide tube positioned inside the first channel, the first guide tube including a proximal end extending toward the surgical robot and a first highly-curved distal end extending away from the surgical robot;

a second guide tube positioned inside the second channel, the second guide tube including a proximal end extending toward the surgical robot and a second highly-curved distal end extending away from the surgical robot;

a first inner tube housed inside the first guide tube, wherein the first inner tube is axially moveable and rotatable relative to the first guide tube;

a first surgical tool disposed in the first inner tube, the first surgical tool protruding from a distal end of the first inner tube;

a first tool cartridge;

a second inner tube housed inside the second guide tube, wherein the second inner tube is axially moveable and rotatable relative to the second guide tube;

a second surgical tool housed inside the second inner tube, the second surgical tool protruding from a distal end of the second inner tube; and a second tool cartridge;

wherein the first tool cartridge controls axial movement and rotation of the first guide tube, wherein the first tool cartridge controls axial movement and rotation of the first inner tube independent of the control of the axial movement and rotation of the first guide tube, wherein the second tool cartridge controls axial movement and rotation of the second guide tube, wherein the second tool cartridge controls axial movement and rotation of the second inner tube independent of the control of the axial movement and rotation of the second guide tube, wherein the first highly-curved distal end of the first guide tube includes a shapeset curvature between about 50 m^(−1) and about 100 m^(−1), wherein the second highly-curved distal end of the second guide tube includes a shapeset curvature between about 50 m^(−1) and about 100 m^(−1), wherein a curvature of the first inner tube is less than the shapeset curvature of the first highly-curved distal end of the first guide tube and less than a curvature of the first channel, wherein the first inner tube straightens the first guide tube towards a longitudinal axis of the first inner tube, forming a first combined effective curvature of the combination of the first guide tube and the first inner tube, wherein the first combined effective curvature is greater than about 40 m^(−1), wherein a curvature of the second inner tube is less than the shapeset curvature of the second highly-curved distal end of the second quide tube and less than a curvature of the second channel, wherein the second inner tube straightens the second guide tube towards a longitudinal axis of the second inner tube, forming a second combined effective curvature of the combination of the second guide tube and the second inner tube, and wherein the second combined effective curvature is greater than about 40 m^(−1).

14. The apparatus of claim 13, wherein:

the shapeset curvature of the first highly-curved distal end of the first guide tube is about 72 m^(−1); and the shapeset curvature of the second highly-curved distal end of the second guide tube is about 72 m^(−1).

15. The apparatus of claim 13, wherein:

the first combined effective curvature is between about 60 m^(−1) and about 65 m^(−1);and the second combined effective curvature is between about 60 m^(−1) and about 65 m^(−1).

16. The apparatus of claim 13, wherein:

the highly curved distal end of the first guide tube includes a double-curvature configuration including a first curved region and a second curved region, wherein the first curved region includes a curvature between about 50 m^(−1) and about 100 m^(−1), and the second curved region includes a curvature between about 35 m^(−1) and about 45 m^(−1); and the highly curved distal end of the second guide tube includes a double-curvature configuration including a third curved region and a fourth curved region, wherein the third curved region includes a curvature between about 50 m^(−1) and about 100 m^(−1), and the fourth curved region includes a curvature between about 35 m^(−1) and about 45 m^(−1).

17. The apparatus of claim 13, wherein the inner sheath is disposed in the outer sheath, wherein the endoscopic device further includes a sheath insert disposed in the inner sheath, and wherein the channel is disposed inside the sheath insert.

18. The apparatus of claim 13, wherein the first channel disposed inside the inner sheath is curved, and wherein the second channel disposed inside the inner sheath is curved.

19. An apparatus for performing surgery, comprising:

a surgical robot including an endoscopic device extending from the surgical robot, the endoscopic device including an outer sheath, an inner sheath and a channel disposed inside the inner sheath;

a guide tube positioned inside the channel, the guide tube including a proximal end extending toward the surgical robot and a highly-curved distal end extending away from the surgical robot;

an inner tube housed inside the guide tube, wherein the inner tube is axially moveable and rotatable relative to the guide tube;

a surgical tool disposed in the inner tube, the surgical tool protruding from a distal end of the inner tube; and a tool cartridge, wherein the tool cartridge controls axial movement and rotation of the guide tube, wherein the tool cartridge controls axial movement and rotation of the inner tube independent of the control of the axial movement and rotation of the guide tube, wherein the highly-curved distal end of the guide tube includes a shapeset curvature between about 50 m^(−1) and about 100 m^(−1), wherein a curvature of the inner tube is less than the shapeset curvature of the highly-curved distal end of the guide tube and less than a curvature of the channel, wherein the inner tube straightens the guide tube towards a longitudinal axis of the inner tube, forming a combined effective curvature of the combination of the guide tube and the inner tube, and wherein the combined effective curvature is between about 40 m^(−1) and about 100 m^(−1).

20. The apparatus of claim 19, wherein the channel disposed inside the inner sheath is curved.

* * * * *